United States Patent [19]

Beeby

[11] 4,094,978
[45] June 13, 1978

[54] 3-PROPENYL DERIVATIVES OF CEPHALOSPORIN, COMPOSITIONS AND THEIR USE

[75] Inventor: Philip J. Beeby, Melbourne, Australia

[73] Assignee: Syntex (U.S.A.) Inc., Palo Alto, Calif.

[21] Appl. No.: 709,696

[22] Filed: Jul. 29, 1976

[51] Int. Cl.$^2$ .................. A61K 31/545; C07D 501/24
[52] U.S. Cl. ...................................... 424/246; 544/16; 544/30; 544/28; 544/22; 542/416; 560/29; 560/39
[58] Field of Search ..................... 424/246; 260/243 C

[56] References Cited
U.S. PATENT DOCUMENTS

| 3,929,780 | 12/1975 | Weir | 260/243 C |
|---|---|---|---|
| 3,983,113 | 9/1976 | Beeby | 260/243 C |
| 3,994,884 | 11/1976 | Weir | 260/243 C |
| 4,012,380 | 3/1977 | Spry | 260/243 C |

Primary Examiner—Nicholas S. Rizzo
Assistant Examiner—David E. Wheeler
Attorney, Agent, or Firm—Gerard A. Blaufarb

[57] ABSTRACT 3-(3-hydroxyprop-1-(t)-enyl)-7β-(α-substituted acetamido)-ceph-3-em-4-carboxylic acids; 3-(3-carbamoyloxyprop-1-(t)-enyl)-7β-(α-substituted acetamido)-ceph-3-em-4-carboxylic acids; and 3-[3-(N-substituted carbamoyloxy)prop-1-(t)-enyl]-7β-(α-substituted acetamido)-ceph-3-em-4-carboxylic acids and derivatives and salts thereof and process for preparing such compounds. The compounds are useful as antibacterials and are active against a wide variety of gram positive and gram negative bacteria.

36 Claims, No Drawings

3-PROPENYL DERIVATIVES OF CEPHALOSPORIN, COMPOSITIONS AND THEIR USE

BACKGROUND OF THE INVENTION

1. The Invention

This invention relates to cephalosporin type compounds, having antibacterial activity and processes for preparing such compounds. In a further aspect, this invention relates to 3-(3-hydroxyprop-1-(t)-enyl)-7β-(α-substituted acetamido)-ceph-3-em-4-carboxylic acids; 3-(3-carbamoyloxyprop-1-(t)-enyl)-7β-(α-substituted acetamido)-ceph-3-em-4-carboxylic acids; and 3-[3-(N-substituted carbamoyloxy)prop-1-(t)-enyl]-7β-(α-substituted acetamido)-ceph-3-em-4-carboxylic acids and to esters and salts thereof; and to methods for preparing such compounds. In a still further aspect, the invention relates to pharmaceutical compositions and antiseptic compositions containing such compounds and to methods of destroying and/or inhibiting the growth of gram negative and/or gram positive bacteria.

2. The Prior Art

Since the first discovery that certain derivatives of Cephalosporin C exhibit potent antibiotic activity, a large number of cephalosporin type compounds have been synthesized for possible improved, or different, antibiotic activity and selectivity (note for example, U.S. Pat. Nos. 3,769,227, 3,830,700, 3,853,860, 3,859,274, 3,864,338 and 3,867,380). A general discussion of cephalosporins can be found in *Cephalosporins and Penicillins Chemistry and Biology*, edit E. H. Flynn, Academic Press, Inc. (1972).

SUMMARY OF THE INVENTION

In summary, the compounds of the invention can be represented by the following generic formula:

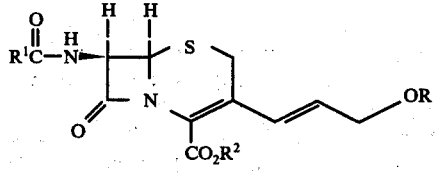

I wherein:
R is hydrogen or a group having the formula

in which $R^3$ is hydrogen, alkyl having one to six carbon atoms, or the group

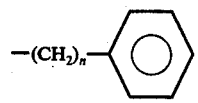

in which $n$ is 0 to 3, inclusive;
$R^1$ is a group having the formula

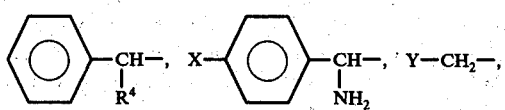

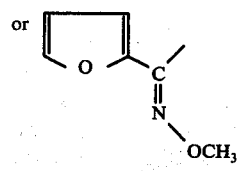

wherein $R^4$ is hydrogen, hydroxy or carboxy; X is hydrogen or hydroxy; Y is thiophen-2-yl, (1H)-tetrazol-1-yl, 4-pyridylthio, phenoxy or cyano; and $R^2$ is hydrogen or a protecting group selected from the group of benzhydryl, benzyl, o-nitrobenzyl, p-nitrobenzyl, 3,5-dinitrobenzyl, p-methoxybenzyl, t-butyl, pivaloyloxymethyl, phenacyl and polyhaloalkyl having two to six carbon atoms.

The pharmaceutically acceptable salts of the above compounds, with respect to the C-4 acid and $R^4$ carboxy moieties, are also encompassed within the scope of the invention. Also, as can be seen from formula I the steric configuration of the propenyl double bond is trans and the substituent at the 7-position is beta oriented.

In summary, one process of the invention comprises hydrolizing a compound of the formula

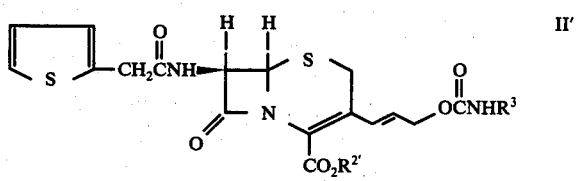

II' wherein $R^3$ is as defined above and $R^{2'}$ is as defined above for $R^2$, but is other than hydrogen.

In summary, another process of the invention comprises hydrolyzing a compound of the formula

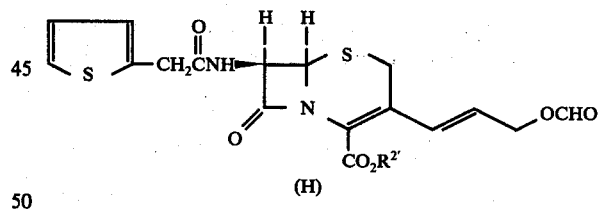

(H)

wherein $R^{2'}$ is as defined above for $R^2$, but is other than hydrogen.

In summary, still another process of the invention comprises hydrolyzing a compound of the formula

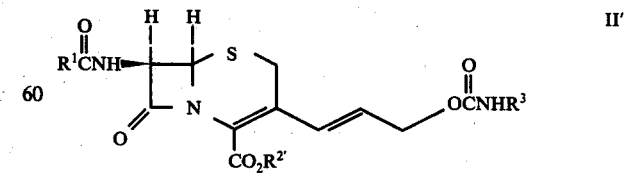

II' wherein $R^1$ and $R^3$ are as defined above and $R^{2'}$ is as defined above for $R^2$, but is other than hydrogen.

In summary, a further process of the invention comprises hydrolyzing a compound of the formula

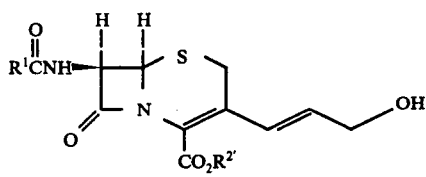

III'

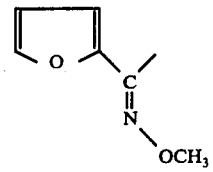

wherein $R^1$ is as defined above and $R^{2'}$ is as defined above for $R^2$, but is other than hydrogen.

In summary, still a further process of the invention comprises optionally converting a free acid, obtained via one of the above processes, to its corresponding pharmaceutically acceptable salt; or optionally converting a pharmaceutically acceptable salt formed in a previous step to its corresponding free acid; or optionally converting a free acid or a pharmaceutically acceptable salt thereof, formed in a previous step, to a suitable ester protecting group.

In summary, the pharmaceutical compositions and antiseptic compositions of the invention, comprise the 4-carboxylic acid compounds of formula I and/or pharmaceutically acceptable salts thereof, and a pharmaceutically acceptable carrier or antiseptic carrier.

In summary, the process of the invention for reducing or inhibiting bacterial infections comprises administering an effective amount of a carboxylic acid of formula I or a pharmaceutically acceptable salt thereof, to mammals suffering from such infections, or in the case of undesired bacterial growth on inanimate objects, applying an effective amount of the aforementioned compounds in an antiseptic carrier to such objects.

The invention will be further described hereinbelow.

FURTHER DESCRIPTION OF THE INVENTION AND PREFERRED EMBODIMENTS

The compounds of the invention can be represented by the following subgeneric formulas:

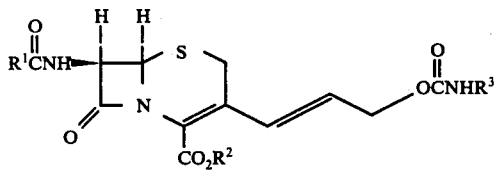

II

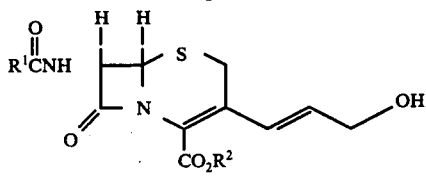

III wherein
$R^1$ is a group having the formula

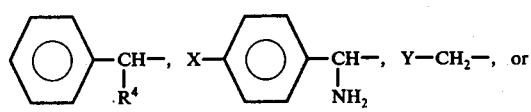

wherein $R^4$ is hydrogen, hydroxy or carboxy; X is hydrogen or hydroxy; Y is thiophen-2-yl, (1H)-tetrazol-1-yl, 4-pyridylthio, phenoxy or cyano;

$R^2$ is hydrogen or a protecting group selected from the group of benzhydryl, benzyl, o-nitrobenzyl, p-nitrobenzyl, 3,5-dinitrobenzyl, p-methoxybenzyl, t-butyl, pivaloyloxymethyl, phenacyl and polyhaloalkyl having two to six carbon atoms; and $R^3$ is hydrogen, alkyl having one to six carbon atoms, or the group

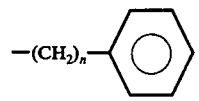

in which n is 0 to 3 inclusive.

Also, encompassed within the invention are the pharmaceutically acceptable salts of compounds of formulas II and III.

Compounds of formulas II and III wherein the $R^1$ moiety contains a free hydroxy, carboxy, or amino group exist as optical isomers; accordingly, the above formulas are intended to represent the respective (D) and (L) optical isomers as well as mixtures thereof and the individual isomers as well as mixtures thereof are encompassed within the invention. Generally, in terms of antibiotic activity, the (D) optical isomers are preferred.

Also, as previously noted, the C-7 position substituent is beta oriented and the propenyl double bond is trans oriented.

Preferred compounds embraced by subgeneric formula II are those wherein $R^3$ is hydrogen or phenyl.

Particularly preferred compounds within the group described in the previous paragraph are those wherein $R^1$ is a group having the formula

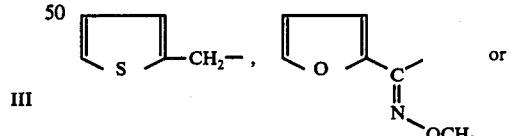

(a)  (b)

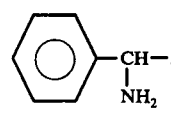

(c)

Thus, one particularly preferred group of compounds are those wherein $R^1=(a)$. Another particularly preferred group of compounds are those wherein $R^1=(b)$. Still another particularly preferred group of compounds are those wherein $R^1=(c)$.

Preferred compounds embraced by subgeneric formula III are those wherein $R^1$ is a group having the formula

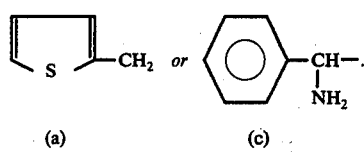

Thus, one preferred group of compounds are those wherein $R^1 = (a)$. Another preferred group of compounds are those wherein $R^1 = (c)$.

In terms of convenience, the sodium salts are preferred, accordingly, the particularly preferred salts are the sodium salts of the preferred and particularly preferred compounds of formulas II and III.

The process of the invention for preparing the compounds of formulas II and III can be schematically represented by the following sequence of overall reaction equations.

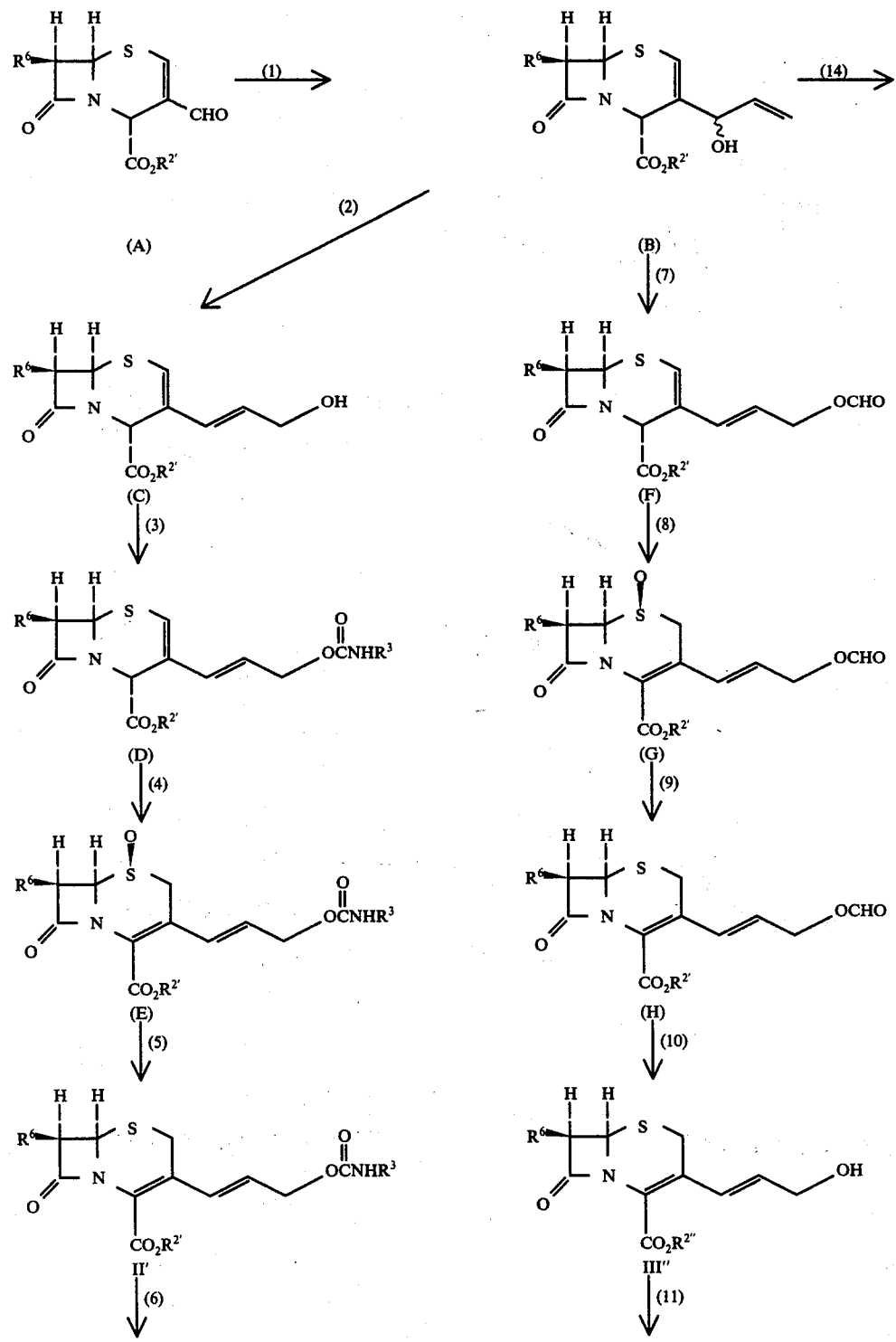

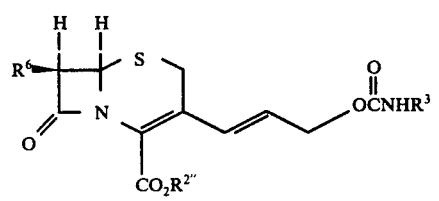
II″
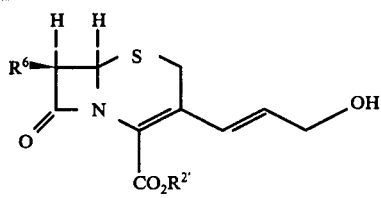
III′
(13)
(12)
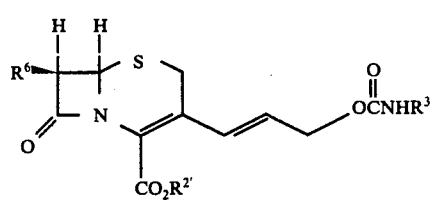
II′
(B) (14) →
(J)
(15)
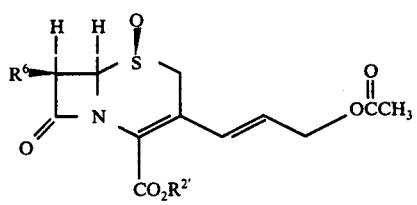
(K)
(16) →
(17)
(L)
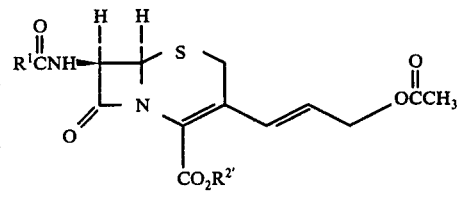
(M)
(N)
III′
(20) ↓
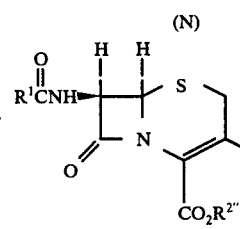
III′
(21) →

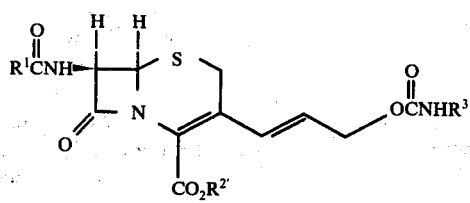

II'

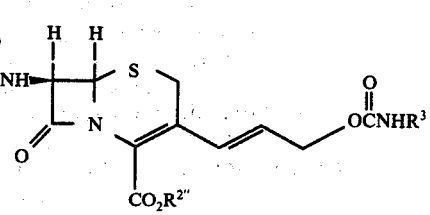

II'' wherein $R^1$ and $R^3$ are as defined above; $R^{2'}$ is a suitable protecting group, e.g. benzhydryl; $R^{2''}$ is hydrogen or a pharmaceutically acceptable cation, e.g. sodium; $R^6$ is thiophen-2-ylacetamido; and the ~OH in the formula B indicates a mixture of α- and β- hydroxy isomers.

Step 1, of the above process, can be conveniently effected by treating the starting material of formula A with a suitable vinyl Grignard reagent, preferably in a suitable inert organic solvent. Typically, this treatment is conducted at temperatures in the range of −100° to −20° C, preferably about from −60° to −80° C, for about from 0.25 to 2.0 hours, and preferably about from 0.25 to 0.5 hours. Typically, a mole ratio of Grignard reagent to compound of formula A of about from 3 to 10, preferably about from 4 to 5, is used. Typically, and preferably, the treatment is conducted uner anhydrous conditions and under an inert atmosphere; e.g. nitrogen. Suitable inert organic solvents which can be used include, for example, tetrahydrofuran, dimethoxyethane, dioxane and the like, and mixtures thereof. Suitable Grignard reagents which can be used include, for example, vinyl magnesium chloride. vinyl magnesium bromide and the like. The resulting product is a mixture of α- and β-hydroxy isomers which, if desired, can be separated by conventional procedures.

The starting materials of formula A are known compounds and can be prepared according to known procedures such as, for example, described in U.S. Pat. No. 3,864,338, and in the Preparations set forth hereinbelow; or by obvious modifications of such procedures; e.g. by substitution of protecting groups.

Step 2, can be effected by treating a compound of formula B with p-toluenesulfonic acid, and water, in an inert organic solvent such as tetrahydrofuran. Typically, this rearrangement is conducted at temperatures in the range of about from 0° to 60° C, preferably about from 20° to 40° C, for about from 1 to 24 hours using mole ratios of p-toluenesulfonic acid to compound of formula B in the range of about from 1:1 to 1:100, preferably from about 1:5 to 1:10, and using mole ratios of water to compound of formula B of about from 1:1 to 50:1. Suitable inert organic solvents which can be used in place of tetrahydrofuran include, for example, dioxane, dimethoxyethane, dichloromethane, chloroform and the like and mixtures thereof. Also, in place of p-toluenesulfonic acid, the following acids could be used: benzenesulfonic acid, perchloric acid, hydrochloric acid, sulfuric acid and the like. Typically best results are obtained using p-toluenesulfonic acid, and tetrahydrofuran as the inert organic solvent.

Step 3, transformation of the 3-hydroxy group to the 3-carbamate group (—OC(O)NR³), can be effected by treating a compound of formula C with chlorosulfonyl isocyanate or a suitable isocyanate having the desired $R^3$ moiety. Typically this treatment is conducted in an inert organic solvent under anhydrous conditions and in an inert atmosphere. Suitable inert organic solvents which can be used include, for example, tetrahydrofuran, dioxane, methylene chloride, chloroform and the like. Tetrahydrofuran is the preferred solvent.

When chlorosulfonyl isocyanate is employed in step 3, the reaction is carried out at temperatures in the range of about from −80° to 0° C, preferably at about −55° C, for about from 5 minutes to 2 hours, preferably about 30 minutes, using mole ratios of chlorosulfonyl isocyanate to compound of formula C in the range of 1:1 to 3:1, preferably about 1:1.

When a suitable isocyanate having the desired $R^3$ moiety is employed in step 3; the reaction is optionally conducted in the presence of a tertiary amine catalyst at temperatures in the range of about from −80° to 100° C, preferably about from 50° to 80° C, for about from 30 minutes to 8 hours, preferably about 2 hours, using mole ratios of isocyanate to compound of formula C in the range of 1:1 to 2:1, preferably about 1:1. Suitable tertiary amine catalysts include trimethylamine, pyridine, N-methylpiperidine and the like.

Rearrangement of the cephem double bond in compounds of formula D proceeds via steps 4 and 5.

Step 4 can be conveniently effected by treating a compound of formula D with m-chloroperbenzoic acid in a suitable inert organic solvent. Typically, this treatment is conducted at temperatures in the range of about from −10° to 25° C, preferably about from 0° to 5° C for about from 0.5 to 24 hours, preferably about from three to five hours, using mole ratios of m-chloroperbenzoic acid to compound of formula D of about from 1.0 to 1.2. Preferably this mole ratio should be close to one (about from 1.05 to 1.1) to prevent over oxidation of the thio moiety to sulfonyl). Suitable inert organic solvents which can be used include, for example, methylene chloride, chloroform, and the like, and mixtures thereof. Also, in place of m-chloroperbenzoic acid, the following reagents could be used: perbenzoic acid, peracetic acid, hydrogen peroxide, sodium metaperiodate, ozone, and the like.

Step 5 can be conveniently effected by treating the sufloxide of formula E with a mixture of stannous chloride and acetyl chloride in a suitable inert organic solvent, preferably under an inert atmosphere. Typically, this treatment is conducted at temperatures in the range of about from −10° to 25° C, preferably from 0° to 5° C for about from 0.25 to 5.0 hours, preferably about from 0.3 to 1.0 hours using mole ratios of stannous chloride to compound of formula E of about from 1.5 to 5.0, and preferably about from 2.0 to 3.0. Also, in place of stannous chloride and acetyl chloride, the following reagents could also be used: phosphorus trichloride, phosphorus tribromide, and the like, and mixtures thereof.

Step 6, removal of the C-4 ester group, can be effected by conventional procedures used in the art to cleave ester groups to yield the corresponding acid. For example, benzhydryl and p-methoxybenzyl can be conveniently cleaved by treatment with a trifluoroacetic acid/anisole mixture (typically 2:1 to 6:1 mole ratio) at 0° – 5° C for about from 2 to 5 minutes, optionally in the presence of an inert organic solvent such as methylene chloride, benzene and the like.

Step 7, transformation of the 1-hydroxyprop-2-enyl group to the 3-formyloxyprop-1-(t)-enyl group, can be effected by treating a compound of formula B with formic acid and p-toluenesulfonic acid in an inert organic solvent. Typically this treatment is conducted at temperatures in the range of about from 0° to 70° C, preferably about from 30° to 40° C, for about from ½ to 12 hours, preferably about from four to eight hours, using mole ratios of formic acid to compound of formula B in the range of about from 5:1 to 500:1, preferably from about 20:1 to 40:1, and mole ratios of p-toluenesulfonic acid to compound of formula B in the range of about from 1:1 to 1:100, preferably about from 1:10 to 1:20. Suitable inert organic solvents which can be used include, for example, tetrahydrofuran, dioxane, dimethoxyethane, dichloromethane, chloroform and the like and mixtures thereof. Also, in place of p-toluenesulfoic acid, the following acids could also be used: benzenesulfonic acid, perchloric acid, hydrochloric acid, sulfuric acid, and the like. Typically, best results are obtained using p-toluenesulfonic acid, and tetrahydrofuran as the inert organic solvent.

Steps 8 and 9, rearrangements of the cephem double bond, are effected by treating compounds of formula F and G, respectively, in the manner previously described in steps 4 and 5 respectively.

Step 10, hydrolysis of the 3-formyloxy group to 3-hydroxy and removal of the C-4 ester group, can be effected by first treating a compound of formula H with a trifluoro acetic acid/anisole mixture (typically 2:1 to 6:1 mole ratio) at 0°–5° C for about from 2 to 5 minutes, optionally in the presence of an inert organic solvent such as methylene chloride, benzene and the like, and thereafter treating the resulting free C-4 acid with an aqueous inorganic base (e.g. aqueous sodium bicarbonate, potassium bicarbonate and the like) at room temperature for about from 1 to 6 hours, preferably about 2 hours, using a mole ratio of bicarbonate to C-4 acid of about 2:1.

Step 11, replacement of the C-4 carboxy protecting group can be effected via conventional procedures; for example, (in the case of benzhydryl protecting groups) by treatment of a compound of formula III″ with about a molar equivalent of diphenyldiazomethane in an inert solvent, such as tetrahydrofuran, ethyl acetate and the like, at 0° to 50° C, preferably about 30° C, for about from 1 to 6 hours, preferably about 3 hours.

Step 12, transformation of the 3-hydroxy group to the 3-carbamate group (—OC(O)NR$^3$), is effected by treating a compound of formula III′ in the manner previously described in step 3.

Step 13, removal of the C-4 ester group, is effected by treating a compound of formula II′ in the manner previously described in step 6.

Step 14, transformation of the 1-hydroxyprop-2-enyl group to the 3-acetoxyprop-1-(t)-enyl group, can be effected by treatment of a compound of formula B with acetic acid and p-toluenesulfonic acid in an inert organic solvent. Typically, this treatment is conducted at temperatures in the range of about from 0° to 70° C, preferably about from 30° to 40° C, for about from ½ to 12 hours, preferably about from 4 to 8 hours, using mole ratios of acetic acid to compound of formula B in the range of about from 5:1 to 500:1, preferably from about 20:1 to 40:1, and mole ratios of p-toluenesulfonic acid to compound of formula B in the range of about from 1:1 to 1:100, preferably about from 1:10 to 1:20. Suitable inert organic solvents which can be used include, for example, tetrahydrofuran, dioxane, dimethoxyethane, dichloromethane, chloroform and the like and mixtures thereof. Also, in the place of p-toluenesulfonic acid, the following acids could also be used: benzenesulfonic acid, perchloric acid, hydrochloric acid, sulfuric acid, and the like. Typically, best results are obtained using p-toluenesulfonic acid, and tetrahydrofuran as the inert organic solvent.

Steps 15 and 16, rearrangement of the cephem double bond, are effected by treating the compounds of formulas J and K in the manner previously described in steps 4 and 5, respectively.

Step 17 of the process can be conveniently effected by treating the compound of formula L with phosphorus pentachloride in an inert organic solvent, in the presence of pyridine. This portion of step 17 is typically conducted under anhydrous conditions and in an inert atmosphere at temperatures in the range of about from 10° to 30° C for about from 2 to 4 hours using 1.2 to 1.25 moles of pyridine and about from 1.1 to 1.2 moles of phosphorous pentachloride per mole of compound of formula L. After the reaction is substantially complete, about from one to 10 moles of isobutyl alcohol, preferably about three to five moles, per mole of formula L is added to the product mixture, and the treatment continued at temperatures in the range of about from −20° to 30° C, preferably about from 0° to 5° C for about from 15 minutes to 2 hours, preferably about from 30 minutes to 1 hour. A small quantity of water is then added to effect the final reaction in this treatment. This final step is typically conducted at temperatures in the range of −20° to 30° C, preferably about from 0° to 5° C for about from 5 minutes to 1 hour, preferably about from 15 to 30 minutes. Suitable inert organic solvents include, for example, methylene dichloride, chloroform, and the like. Also, in place of pyridine, the following compounds can be used, for example, quinoline, N,N-dimethylaniline, and the like. Also, in place of isobutyl alcohol, other lower alkanols can be used, for example, methanol, ethanol, and the like or mixtures thereof.

Step 18, acylation of the C-7 amino group, can be effected by conventional amino acylation procedures. For example, step 18 can be conveniently effected by treating a compound of formula M with about from 1.1 to 1.5 stoichiometric equivalents of an acid halide, having the desired $R^1$ moiety in an inert organic solvent (e.g. dichloromethane, chloroform, etc.) in the presence of an organic or inorganic base (e.g. sodium bicarbonate, pyridine, triethylamine and the like). Typically, this treatment is conducted at temperatures in the range of from about 0° to 5° C for about from 30 minutes to 1 hour. Typically, about from two to 10 stoichiometric equivalents of the base is used. The acylation can also be effected via treatment with a carboxy acid, having the desired $R^1$ moiety (i.e. $R^1$ COOH) and a suitable coupling reagent (e.g., dicyclohexyl carbodiimide or N-ethoxycarbonyl-2-ethoxy-1,2-dihydroquinoline) in a suitable inert organic solvent, e.g. dichloromethane.

When the $R^1$ moiety of the acylating agent is a group of the formula

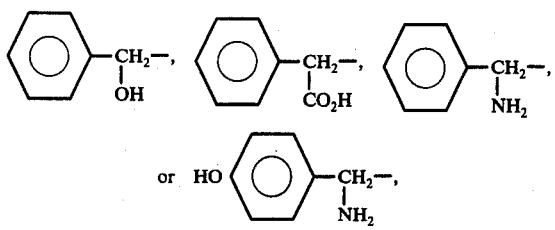

it is preferred that the hydroxy, carboxy and amino functions in the group be protected with a suitable protecting group which can be easily removed in the last step (e.g. 21 or 22) of the process.

For example, α-hydroxy compounds can be conveniently prepared via acylation with α-(methoxymethoxy)phenylacetyl halide to yield the corresponding protected hydroxy derivative. Similarly, α-carboxy compounds can be prepared by acylation with α-(tert-butoxycarbonyl)phenyl acetic acid to yield the corresponding tert-butoxy protected α-carboxy derivative. In like manner, α-amino compounds can be prepared via acylation with α-(tert-butoxycarbonylamino)-α-phenylacetic acid to yield the corresponding t-butoxycarbonyl protected α-amino derivative. Moreover, α-amino-α-(4-hydroxyphenyl) compounds can be prepared by acylation with α-(tert-butoxycarbonylamino)-α-(4-methoxymethoxy)acetyl chloride.

If the optical isomers of compounds of formulas II'' and III'' (wherein $R^4$ is hydroxy, carboxy or amino) are desired, they can be conveniently prepared by using the corresponding optically active acid halide or acid in the acylation step (step 18). In the case of the compounds of formula II'' and III'' wherein $R^4$ is carboxy, a reaction equilibrium exists between the respective D and L optical isomers and hence in this case the stable compound will exist as a mixture of the D and L isomers.

Step 19, hydrolysis of the 3-acetoxy group to 3-hydroxy, can be effected by treating a compound of formula N with aqueous inorganic base (e.g., sodium carbonate, sodium bicarbonate or sodium hydroxide) in a water miscible organic solvent. Typically, this treatment is conducted at temperatures in the range of about from 0° to 80° C, preferably from 0° to 40° C, for about from 1 to 24 hours, preferably about 2 hours, using a ole ratio of carbonate (or bicarbonate) to compound of formula N of about 1:2 and using a mole ratio of sodium hydroxide to compound of formula N of about 1:1. Suitable water miscible solvents include acetone, methanol, ethanol, dimethoxyethane and the like. Alternatively step 19 can be effected by treating a compound of formula N with citrus acetyl enzyme as described by J.D'A. Jeffery et al. in the Biochemical Journal, 81, 591 (1961).

Step 20, transformation of the 3-hydroxy group to the 3-carbamate group (—OC(O)NR$^3$), can be effected by treating a compound of formula III' in the manner previously described in step 3.

Steps 21 and 22 are both directed to removal of the C-4 ester group and deprotection, if necessary, of the $R^1$ moiety of the 7β-substituent.

(A) When the 7β-substituent in compounds of formula II' and III' is phenylacetamido, (1H)-tetrazol-1-ylactamido, 4-pyridylthioacetamido, phenoxyacetamido, cyanoacetamido or 2-methoxyimino(fur-2-yl)acetamido, steps 21 and 22 can be effected by conventional procedures used in the art to cleave ester groups. For example, benzhydryl and p-methoxybenzyl can be cleaved via treatment with a trifluoroacetic acid/anisole mixture (typically 2:1 to 6:1 mole ratio) at 0°–5° C for about from 2 to 5 minutes optionally in the presence of an inert solvent, e.g., methylene chloride, benzene, and the like.

(B) When the 7β-substituent in compounds of formulas II' and III' is α-(tert-butoxycarbonyl)-α-phenylacetamido or α-(tert-butoxycarbonylamino)-α-phenylacetamido, steps 21 and 22 (can be effected as described in paragraph A above) however, treatment is extended from 2 to 5 minutes to 30 to 120 minutes.

(C) When the 7β-substituent in compounds of formulas II' and III' is α-(methoxymethoxy)-α-phenylacetamido, steps 21 and 22 can be effected by treatment with an aqueous inorganic acid (e.g. hydrochloric acid, sulfuric acid and the like) in a water miscible solvent such as acetone, methanol, ethanol, tetrahydrofuran and the like followed by treatment in the manner described in paragraph A above. Typically, the first part of the treatment is conducted at temperatures in the range of about from 0° to 30° C, preferably at 20° C, for about from 30 minutes to 2 hours using mole ratios of hydrochloric acid to compound of formula II' or III' of about from 0.01 to 0.5.

(D) When the 7β-substituent in compounds of formulas II' and III' is α-(tert-butoxycarbonylamino-α-(4-methoxymethoxyphenyl) acetamido, steps 21 and 22 can be effected by treatment with aqueous acid as described in paragraph C followed by treatment in the manner described in paragraph B.

It is generally preferred that the respective product of each process step, described hereinabove, be separated and/or isolated prior to its use as a starting material in subsequent steps. Separation and isolation can be effected by any suitable purification procedure such as, for example, evaporation, crystallization, column chromatography, thin-layer chromatography, distillation, etc. Specific illustrations of typical separation and isolation procedures can be had by reference to the appropriate examples described hereinbelow; however other equivalent separation procedures could, or course, also be used. Also, it should be appreciated that where typical reaction conditions (e.g. temperatures, mole ratios, reaction times) have been given that conditions both above and below these ranges can also be used, though generally less conveniently.

The pharmaceutically acceptable salts, of the invention, can be prepared according to procedures which are well known in the art, for example, by simply treating the free acid of formulas II'' and III'' with an inorganic or organic base having the desired salt cation, e.g. sodium hydroxide, potassium hydroxide, triethylamine, ethanolamine, tris(hydroxymethyl) aminomethane, etc. The sodium salts can also be conveniently prepared by treating a solution of the acid in ethyl acetate with an excess of sodium 2-ethylhexanoate.

The compounds of the invention and salts thereof, have a broad spectrum of antibacterial activity against both gram positive and gram negative organisms such as *Staphylococcus aureaus, Proteus vulgaris, Escherichia coli, Streptococcus pyogenes, Klebsiella pneumoniae,* and *Shigella sonnei*. The compounds can be used to combat or prophylactically to prevent infections of this nature in mammals and can be administered in the same manner as cephalothin or cephalosporin derivative drugs are generally administered (typically parenterally or orally). The compounds can be administered in a wide variety of dosage forms, either alone or in combination with other pharmaceutically compatible medicaments, in the form of pharmaceutical compositions suited for oral or parenteral administration. The dosage forms typically comprise the compounds (typically as pharmaceutically acceptable salts) and a pharmaceutically carrier and are preferably formulated in unit dosage form to facilitate the simple administration of precise dosages. The pharmaceutical carrier can be either a solid material or liquid, in which the compound is dissolved, dispersed or suspended. The dosage form can optionally contain other compatible medicaments, preservatives, emulsifying agents, wetting agents and/or pH-buffering agents. Suitable preservatives which can be used include, for example, benzyl alcohol and the like. Suitable buffering agents include, for example, sodium acetate and pharmaceutical phosphate salts and the like. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like.

The compounds of this invention are typically administered in dosages of about from 10 to 100 mg. per kg. per day of body weight. The precise effective dosage will, of course, vary depending upon the mode of administration, the condition being treated and the host.

The compounds can also be used as antiseptic agents in cleaning or disinfecting compositions, typically in solution form or suspended in a liquid carrier or in an aerosol spray.

Definitions

The following terms, as used hereinabove and below, have the following meaning unless expressly stated to the contrary. The term alkyl refers to a saturated, unbranched, or branched acyclic hydrocarbon group containing 1 to 6 carbon atoms, such as methyl, ethyl, n-propyl, isopropyl, n-butyl, isobutyl, tert-butyl, n-pentyl, n-hexyl, and the like. The term polyhaloalkyl refers to a halo substituted alkyl having from one to six carbon atoms and containing at least two halogen atoms. The term halo or halide refers fluoro, chloro, bromo, or iodo or the corresponding halides. The term pharmaceutically acceptable salts refers to those salts of the parent compound which do not adversely affect the pharmaceutical properties (e.g. toxicity, effectiveness, etc.) of the parent compound such as, for example, are conventionally used in the pharmaceutical art. The salts of the present invention are pharmaceutically acceptable cation salts, with respect to the acid moiety and in cases where $R^4$ is carboxy can be prepared as both mono and bis salts. Suitable pharmaceutically acceptable cations include, for example, the alkali metals, e.g. sodium potassium, etc.; alkaline earth metals, e.g. calcium, etc.; ammonia; organic salts of triethylamine, diethylamine, tris (hydroxymethyl)aminomethane, ethanolamine, choline, caffeine and the like.

The term benzhydryl refers to the radical having the formula

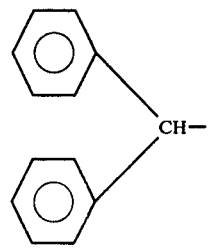

The term (1H)-tetrazol-1-yl refers to the radical having the formula

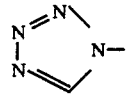

The term methoxyimino-(fur-2-yl) acetamido refers to the syn(cis) isomeric form as regards the configuration of the methoxy group with respect to the carboxamido group. In this specification, the syn configuration is structurally denoted thus:

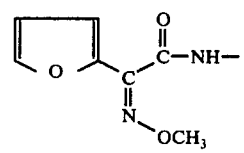

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

A further understanding of the invention can be had from the following non-limiting preparations and examples. Wherein proton magnetic resonance spectrum (n.m.r.) are determined at 100 mHz (the signs of the coupling constants are not assigned) and signals are assigned as singlets (s), broad singlets (bs), doublets (d), double doublets (dd), triplets (t), double triplets (dt), quartets (q) and multiplets (m).

PREPARATION 1

3-Acetoxymethyl-7β-(thiophen-2-yl-acetamido)-ceph-2-em-4-carboxylic acid

In this preparation 42 g. of cephalothin (i.e. 3-acetoxymethyl-7β-(thiophen-2-yl-acetamido)-ceph-3-em-4-carboxylic acid) is dissolved with warming in 130 ml. pyridine, and then cooled to about 18° C. 13 Ml. of acetic anhydride is added and the resulting mixture allowed to stand for 2 hours at room temperature affording a crystalline precipiate. Then 250 ml. of a 65:35, by vol., ethyl ether/ethyl acetate mixture is added and the resulting mixture stirred for one hour and then filtered. The recovered crystals are washed with 65 ml. of 65:35, by vol., ethyl acetate/ethyl ether solution and dried under vacuum to give 41 g. of the pyridinium salt of 3-acetoxymethyl-7β-(thiophen-2-yl-acetamido)-ceph-2-em-4-carboxylic acid. This salt is added to a mixture of 650 ml. water and 650 ml. ethyl acetate and the mixture then acidified to pH 2 using 20% aqueous hydrochloric acid. The ethyl acetate layer is separated and the aqueous layer further extracted with 400 ml. ethyl acetate. The combined ethyl acetate extracts are washed twice with brine, dried over anhydrous sodium sulfate and the solvent then removed under reduced pressure to afford 34 g. of 3-acetoxymethyl-7β-(thiophen-2-yl-acetamido)-ceph-2-em-4-carboxylic acid.

PREPARATION 2

3-Hydroxymethyl-7β-(thiophen-2-yl-acetamido)-ceph-2-em-4-carboxylic acid

In this preparation 34 g. of 3-acetoxymethyl-7β-(thiophen-2-yl-acetamido)-ceph-2-em-4-carboxylic acid is added to a solution of 8.4 g. of lithium hydroxide monohydrate in 1000 ml. of water. The mixture is stirred at room temperature under nitrogen for 2 hours and then layered with 600 ml. of ethyl acetate. The pH of the mixture is then readjusted to pH 2 by the addition of 20% aqueous hydrochloric acid (~50 ml.). The ethyl acetate layer is separated and the aqueous layer is extracted twice with 500 ml. portions of ethyl acetate. The combined ethyl acetate extracts are washed twice with brine, dried over anhydrous sodium sulfate and evaporated to dryness under reduced pressure affording 24.2 g. of 3-hydroxymethyl-7β-(thiophen-2-yl-acetamido)-ceph-2-em-4-carboxylic acid.

PREPARATION 3

Benzhydryl 3-hydroxymethyl-7β-(thiophen-2-yl-acetamido)-ceph-2-em-4-carboxylate In this preparation 24.2 g. of 3-hydroxymethyl-7β-(thiophen-2-yl-acetamido)-ceph-2-em-4-carboxylic acid is dissolved in 800 ml. of tetrahydrofuran, and then 15 g. of diphenyldiazomethane is added and the resulting mixture stirred at room temperature for 3 hours. The mixture is evaporated to dryness under reduced pressure and 250 ml. of 90:10, vol., ethyl ether/methylene chloride solution is added to the residue. After the mixture is stirred for 4 hours, the solid is recovered by filtration, and washed with 100 ml. of 90:10 ethyl ether/methylene chloride and then dried affording 28.5 g. of benzhydryl 3-hydroxymethyl-7β-(thiophen-2-yl-acetamido)-ceph-2-em-4-carboxylate.

PREPARATION 4

Benzhydryl 3-formyl-7β-(thiophen-2-yl-acetamdido)-ceph-2-em-4-carboxylate.

In this preparation 31 g. of dried chromium trioxide is added to a mixture of 51 g. of dry pyridine and 800 ml. of dry methylene chloride and stirred at 15° C under nitrogen for 20 minutes. 26 Grams of benzhydryl 3-hydroxymethyl-7β-(thiophen-2-yl-acetamido)-ceph-2-em-4-carboxylate in 250 ml. of dry methylene chloride is added in one portion. The resulting mixture is stirred for 30 minutes and then filtered through diatomaceous earth. The contents of the reaction flask and the diatomaceous earth are washed with 500 ml. of methylene chloride and combined with the preceding filtrate and then washed with 400 ml. of 5% aqueous potassium hydroxide solution, 500 ml. of 20% aqueous hydrochloric acid and twice with 400 ml. brine. The aqueous washings are back extracted with 500 ml. of methylene chloride and the extracts added to the previously washed methylene chloride filtrate, then dried over sodium sulfate and then stirred for one hour with 30 g. of silica gel. The mixture is filtered and the silica gel washed with 400 ml. 1:1 vol. ethyl acetate/methylene chloride. The combined filtrates are evaporated to dryness under reduced pressure and the resulting residue (26 g.) is recrystallized from ethyl ether/methylene chloride affording 21.4 g. of benzhydryl 3-formyl-7β-(thiophen-2-yl-acetamido)-ceph-2-em-4-carboxylate.

PREPARATION 5

α-(Methoxymethoxy)phenylacetyl chloride

In this preparation 2.4 g. of sodium hydride is added to a solution of 16.6 g. of methyl mandelate in 200 ml. of dimethylformamide. The solution is then stirred at room temperature under nitrogen until hydrogen evolution ceases and then 8.8 g. of chloromethyl methyl ether is added. The resulting mixture is warmed at 60° C for 3 hours and then diluted with aqueous sodium carbonate and extracted with ether. The ether extract is washed with water, dried and evaporated to afford methyl α-(methoxymethoxy)phenyl acetate.

The above obtained ester (2.1 g.) is refluxed for 6 hours in 100 ml. of 5% aqueous sodium carbonate. The resulting solution is cooled, washed with ether and the aqueous layer acidified to a pH of 4 with 1N hydrochloric acid. Thereafter the aqueous layer is rapidly extracted with ether and the ether extract washed with water, dried and evaporated to afford α-(methoxymethoxy)phenyl acetic acid.

The above obtained acid (1.96 g.) is added to a solution of 0.84 g. of sodium bicarbonate in 25 ml. of water and stirring is maintained until a clear solution results. The solution is then evaporated to dryness and the residue dried under vacuum at 80° C to afford sodium α-(methoxymethoxy)phenyl acetate. The salt (1.0 g.) is suspended in 25 ml. of dry benzene (containing 1 drop of pyridine) at 0° C and 1 ml. of distilled oxalyl chloride is then added. The resulting mixture is stirred for 3 hours and then filtered and evaporated to dryness to afford α-(methoxymethoxy)phenylacetyl chloride.

PREPARATION 6

α-(Tert-butoxycarbonylamino)-α-(4-methoxymethoxyphenyl)acetyl chloride

In this preparation 1.81 g. of methyl α-amino-α-(4-hydroxyphenyl)acetate is dissolved in 10 ml. of dimethylformamide under nitrogen and 0.24 g. of sodium hydride is then added. The solution is stirred at room temperature under nitrogen until hydrogen evolution ceases and then 0.80 g. of chloromethyl methyl ether is added. The resulting mixture is warmed at 60° C for 1 hour and then cooled and diluted with water. The aqueous mixture is extracted with ether and the ether extract is dried and evaporated to afford methyl α-amino-α-(4-methoxymethoxyphenyl)acetate.

To a solution of 1 g. of the above obtained ester in 10 ml. of dioxane is added 1 g. of tert-butylazidoformate in 10 ml. of dioxane. The resulting mixture is allowed to stand at room temperature for 16 hours and is then evaporated to dryness to afford methyl α-(tert-butoxycarbonylamino)-α-(4-methoxymethoxyphenyl)acetate.

The above obtained ester (0.5 g.) is refluxed for 6 hours in 50 ml. of 5% aqueous sodium carbonate. The resulting solution is cooled and washed with ethyl acetate and the aqueous layer acidified to a pH of 4 with 1N hydrochloric acid. Thereafter the aqueous layer is rapidly extracted with ethyl acetate to afford α-(tert-butoxycarbonylamino)-α-(4-methoxymethoxyphenyl)acetic acid.

The above obtained acid (0.5 g.) is added to a solution of 0.14 g. of sodium bicarbonate in 10 ml. of water and stirring is maintained until a clear solution results. The solution is then evaported to dryness and the residue is dried under vacuum to afford sodium α-(tert-butoxycrbonylamino)-α-(4-methoxymethoxyphenyl)acetate.

The resulting salt (0.5 g.) is suspended in 25 ml. of dry benzene (containing a trace of pyridine) and 0.5 ml. of distilled oxalyl chloride is then added. The mixture is stirred for 3 hours at 10° C and then filtered and evaporated to dryness to afford α-(tert-butoxycarbonylamino)-α-(4-methoxymethoxyphenyl)acetyl chloride.

EXAMPLE 1

This example illustrates step 1 of the process of the invention. In this example 2.5 g. of benzhydryl 3-formyl-7β-(thiophen-2-yl-acetamido)-ceph-2-em-4-carboxylate in 50 ml. of anhydrous tetrahydrofuran is stirred under nitrogen at −70° C and 10 ml. of a 2.5 molar solution of vinyl magnesium chloride is added dropwise over five minutes. After 15 minutes, 50 ml. of pH 7 buffer solution of dibasic sodium phosphate and monobasic potassium phosphate is added to the well stirred mixture, which is then warmed to room temperature. The mixture is diluted with 200 ml. of water and layered with 200 ml. of ethyl acetate. The pH of the aqueous layer is adjusted to pH 4 by the addition of 20% aqueous hydrochloric acid. The ethyl acetate layer is separated and the aqueous layer extracted with 100 ml. ethyl acetate. The ethyl acetate extracts are combined and then washed twice with 50 ml. portions of brine, dried over sodium sulfate and evaporated under reduced pressure affording benzhydryl 3-(1-hydroxyprop-2-enyl)-7β-(thiophen-2-yl-acetamido)-ceph-2-em-4-carboxylate as a pale yellow oil (2.7 g.).

The two isomers (α-hydroxy and β-hydroxy) are separated using thick-layer or column chromatography on silica gel using 45:5 vol./vol. of methylene chloride/acetone. They are then characterized by their nmr spectra (both oils).

Isomer 1 (higher Rf), nmr (CDCl$_3$) δ:3.78 (s, 2H); 4.596(bd, J 14Hz, 1H); 4.9–5.7 (m, 6H); 6.366 (s, 1H); 6.7–7.5 (m, 14H) ppm.

Isomer 2 (lower Rf), nmr (CDCl$_3$) δ:3.79 (s, 2H); 4.63 (m, 1H); 5.0–5.8 (m, 6H); 6.25 (s, 1H) 6.8–7.5 (m, 14H) ppm.

EXAMPLE 2

This example illustrates step 2 of the process of the invention. In this example a solution of 0.5 g. of benzhydryl 3-(1-hydroxyprop-2-enyl)-7β-(thiophen-2-ylacetamido)-ceph-2-em-4-carboxylate in 10 ml. of tetrahydrofuran and 1 ml. of water is treated with about 50 mg. of p-toluenesulfonic acid and the resulting mixture stirred at room temperature. The reaction is monitored using thin-layer chromatography. When a mole ratio of about 2:1 of unrearranged 1-hydroxyprop-2-enyl to benzhydryl 3-(3-hydroxyprop-1-(t)-enyl)-7β-(thiophen-2-ylacetamido)-ceph-2-em-4-carboxylate is indicated (about 12 hours), the mixture is diluted with water and extracted twice with ethyl acetate. The combined ethyl acetate extracts are washed with dilute aqueous sodium bicarbonate solution and then brine, dried over anhydrous sodium sulfate and evaporated to dryness under reduced pressure to give 0.45 g. of yellow oil. The oil is chromatographed on silica gel eluting with dichloromethane/acetone 9:1 to give 0.22 g. of benzhydryl 3-(1-hydroxyprop-2-enyl)-7β-(thiophen-2-ylacetamido)-ceph-2-em-4-carboxylate and 0.11 g. of benzhydryl 3-(3-hydroxyprop-1-(t)-enyl)-7β-(thiophen-2-ylacetamido)-ceph-2-em-4-carboxylate as a colorless oil; nmr (CDCl$_3$)δ: 3.79 (s, 2H); 3.96 (bd, J 5 Hz, 2H); 5.16 (d, J 4 Hz, 1H); 5.24 (bs, 1H); 5.52 (dd, J 4, 8.5 Hz, 1H); 5.71 (dt, J 5, 16 Hz, 1H); 6.11 (d, J 16 Hz, 1H); 6.22 (s, 1H); 6.7–7.5 (m, 15H)ppm.

EXAMPLE 3

This example illustrates step 3 of the process of the invention for preparing compounds of formula D wherein R$^3$ is hydrogen. In this example a solution of 70 mg. of benzhydryl 3-(3-hydroxyprop-1-(t)-enyl)-7β-(thiophen-2-ylacetamido)ceph-2-em-4-carboxylate in 5 ml. of dry tetrahydrofuran is stirred under nitrogen at −50° C and 30 μl. of chlorosulfonyl isocyanate is added. Stirring is continued for 1 hour while the mixture is warmed to −20° C. Thereafter, 5 ml. of pH 7 buffer (sold by Scientific Products of McGaw Park, Ill.) and 25 ml. of ethyl acetate are added and the mixture is stirred for 15 minutes at room temperature. The ethyl acetate layer is then separated, washed with brine, dried over sodium sulfate and evaporated. The resulting noncrystalline solid is chromatographed on silica gel eluting with 10% acetone in dichloromethane to afford benzhydryl 3-(3-carbamoyloxyprop-1-(t)-enyl)-7β-(thiophen-2-ylacetamido)-ceph-2-em-4-carboxylate as an amorphous solid; ir (KBr): 1780, 1740, 1650–1700 cm$^{-1}$; nmr (CDCl$_3$) δ:3.82 (2H, s); 4.44 (2H, d, J 6Hz); 4.7 (2H, bs); 5.15–5.25 (2H, m); 5.50 (1H, dd, J 4, 8Hz); 5.68 (1H, dt, J 15.5, 6Hz); 6.13 (1H, d, J15.5Hz); 6.25 (1H, s); 6.7 (1H, d, J 8Hz); 6.8–7.5 (14H, m) ppm.

EXAMPLE 3A

This example illustrates step 3 of the process of the invention for preparing the compounds of formula D wherein R$^3$ is other than hydrogen. In this example 0.26 g. of benzhydryl 3-(3-hydroxyprop-1-(t)-enyl)-7β-thiophen-2-ylacetamido)ceph-2-em-4-carboxylate, 0.065 g. of phenyl isocyanate and 5 ml. of tetrahydrofuran are heated at 60° C for 8 hours. Thereafter the reaction mixture is diluted with water and extracted several times with ethyl acetate. The combined ethyl acetate extracts are washed with water, dried over sodium sulfate, and evaporated to dryness. The residue is chromatographed on silica gel eluting with 10% acetone in methylene chloride to afford benzhydryl 3-[3-(N-phenylcarbamoyloxy)-prop-1-(t)-enyl]-7β-(thiophen-2-ylacetamido)-ceph-2-em-4-carboxylate.

Similarly, by following the same procedure but replacing phenyl isocyanate with the reagents listed in Table A, the corresponding compounds listed in Table B are prepared:

TABLE A methyl isocyanate
ethyl isocyanate
n-propyl isocyanate
isopropyl isocyanate
n-butyl isocyanate
isobutyl isocyanate
tert-butyl isocyanate
n-pentyl isocyanate
n-hexyl isocyanate
benzyl isocyanate phenethyl isocyanate
3-phenylpropyl isocyanate

TABLE B benzhydryl 3-[3-(N-methylcarbamoyloxy)prop-1-(t)-enyl]-7β-(thiophen-2-ylacetamido)-ceph-2-em-4-carboxylate, benzhydryl 3-[3-(N-ethylcarbamoyloxy)prop-1-(t)-enyl]-7β-(thiophen-2-ylacetamido)-ceph-2-em-4-carboxylate, benzhydryl 3-[3-(N-n-propylcarbamoyloxy)prop-1-(t)-enyl]-7β-(thiophen-2-ylacetamido)-ceph-2-em-4-carboxylate, benzhydryl 3-[3-(N-isopropylcarbamoyloxy)prop-1-(t)-enyl]-7β-(thiophen-2-ylacetamido)-ceph-2-em-4-carboxylate, benzhydryl 3-[3-(N-n-butylcarbamoyloxy)prop-1-(t)-enyl]-7β-(thiophen-2-ylacetamido)-ceph-2-em-4-carboxylate, benzhydryl 3-[3-(N-isobutylcarbamoyloxy)prop-1-(t)-enyl]-7β-(thiophen-2-ylacetamido)-ceph-2-em-4-carboxylate, benzhydryl 3-[3-(N-tert-butylcarbamoyloxy)prop-1-(t)-enyl]-7β-(thiophen-2-ylacetamido)-ceph-2-em-4-carboxylate, benzhydryl 3-[3-(N-n-pentylcarbamoyloxy)prop-1-(t)-enyl]-7β-(thiophen-2-ylacetamido)-ceph-2-em-4-carboxylate, benzhydryl 3-[3-(N-n-hexylcarbamoyloxy)prop-1-(t)-enyl]-7β-(thiophen-2-ylacetamido)-ceph-2-em-4-carboxylate, benzhydryl 3-[3-(N-benzylcarbamoyloxy)prop-1-(t)-enyl]-7β-(thiophen-2-ylacetamido)-ceph-2-em-4-carboxylate, benzhydryl 3-[3-(N-phenethylcarbamoyloxy)prop-1-(t)-enyl]-7β-(thiophen-2-ylacetamido)-ceph-2-em-4-carboxylate, and benzhydryl 3-{3-[N-(3-phenyl)propylcarbamoyloxy]-prop-1-(t)-enyl}-7β-(thiophen-2-ylacetamido)-ceph-2-em-4-carboxylate.

EXAMPLE 4

This example illustrates steps 4 and 5 of the process of the invention. In this example 350 mg. of benzhydryl 3-(3-carbamoyloxyprop-1-(t)-enyl)-7β-(thiophen-2-ylacetamido)-ceph-2-em-4-carboxylate in 20 ml. methylene chloride is stirred at room temperature and 140 mg. of m-chloroperbenzoic acid is added over a one hour period. The mixture is then diluted with 10 ml. of a saturated aqueous sodium bicarbonate solution and extracted with three 15 ml. portions of ethyl acetate. The ethyl acetate extracts are combined and washed with brine, dried over sodium sulfate, filtered and evaporated to dryness to afford benzhydryl 3-(3-carbamoyloxyprop-1-(t)-enyl)-7β-(thiophen-2-ylacetamido)-ceph-3-em-4-carboxylate-1-oxide.

A solution of the above obtained 1-oxide in approximately 5 ml. of dimethylformamide is stirred at 0° C under nitrogen and 300 mg. of anhydrous stannous chloride and 0.6 ml. of acetyl chloride are added. The mixture is stirred at 0° C for 20 minutes and then at room temperature for 20 minutes. The mixture is diluted with water and extracted twice with ethyl acetate. The combined extracts are washed with brine, dried over anhydrous sodium sulfate, filtered and evaporated to dryness to afford an oily residue. The residue is purified using thick-layer chromatography on silica gel eluting with 20% acetone in methylene chloride. The eluate is treated with ether whereby approximately 200 mg. of a solid crystalline material is obtained. The material is recrystallized from acetone/hexane to afford benzhydryl 3-(3-carbamoyloxyprop-1-(t)-enyl)-7β-(thiophen-2-ylacetamido)-ceph-3-em-4-carboxylate; mp 194°–196° C; $[\alpha]_D$ −89° (dioxane); uv(EtOH): 298 nm ($\epsilon$ 16,600); ir (KBr): 1780, 1720, 1705, 1660 cm$^{-1}$; nmr (DMSO-d$_6$) $\epsilon$: 3.73 (2H, ABq, J 17Hz,); 3.75 (2H, s,); 4.38 (2H, d, J6Hz,); 5.17 (1H, d, J 4Hz); 5.73 (1H, dd, J 4, 8Hz,); 6.47 (2H, bs); 6.5–7.5 (15H, m); 9.16 (1H d, J 8Hz, NH) ppm, Anal. Found: C, 61.41; H, 4.46; N, 7.08%. $C_{30}H_{27}N_3O_6S_2$ requires C, 61.11; H, 4.62; N, 7.13%.

Similarly, by following the same procedure but using the products obtained in Example 3A as starting materials, the following compounds are prepared:

benzhydryl 3-[3-(N-methylcarbamoyloxy)prop-1-(t)-enyl]-7β-(thiophen-2-ylacetamido)-ceph-3-em-4-carboxylate, benzhydryl 3-[3-(N-ethylcarbamoyloxy)prop-1-(t)-enyl]-7β-(thiophen-2-ylacetamido)-ceph-3-em-4-carboxylate, benzhydryl 3-[3-(N-n-propylcarbamoyloxy)prop-1-(t)-enyl]-7β-(thiophen-2-ylacetamido)-ceph-3-em-4-carboxylate, benzhydryl 3-[3-(N-isopropylcarbamoyloxy)prop-1-(t)-enyl]-7β-(thiophen-2-ylacetamido)-ceph-3-em-4-carboxylate, benzhydryl 3-[3-(N-n-butylcarbamoyloxy)prop-1-(t)-enyl]-7β-(thiophen-2-ylacetamido)-ceph-3-em-4-carboxylate, benzhydryl 3-[3-N-isobutylcarbamoyloxy)prop-1-(t)-enyl]-7β-(thiophen-2-ylacetamido)-ceph-3-em-4-carboxylate, benzhydryl 3-[3-(N-tert-butylcarbamoyloxy)prop-1-(t)-enyl]-7β-(thiophen-2-ylacetamido)-ceph-3-em-4-carboxylate, benzhydryl 3-[3-(N-n-pentylcarbamoyloxy)prop-1-(t)-enyl]-7β-(thiophen-2-ylacetamido)-ceph-3-em-4-carboxylate, benzhydryl 3-[3-(N-n-hexylcarbamoyloxy)prop-1-(t)-enyl]-7β-(thiophen-2-ylacetamido)-ceph-3-em-4-carboxylate, benzhydryl 3-[3-(N-benzylcarbamoyloxy)prop-1-(t)-enyl]-7β-(thiophen-2-ylacetamido)-ceph-3-em-4-carboxylate, benzhydryl 3-[3-(N-phenethylcarbamoyloxy)prop-1-(t)-enyl]-7β-(thiophen-2-ylacetamido)-ceph-3-em-4-carboxylate, benzhydryl 3-{3-[N-(3-phenylpropyl)carbamoyloxy]-prop-1-(t)-enyl}-7β-(thiophen-2-ylacetamido)-ceph-3-em-4-carboxylate, and benzhydryl 3-[3-(N-phenylcarbamoyloxy)prop-1-(t)-enyl]-7β-(thiophen-2-ylacetamido)-ceph-3-em-4-carboxylate.

EXAMPLE 5

This example illustrates step 6 of the process of the invention. In this example, 120 mg. of benzhydryl 3-(3-carbamoyloxyprop-1-(t)-enyl)-7β-(thiophen-2-ylacetamido)-ceph-3-em-4-carboxylate and 0.5 ml. of anisole are stirred together at 0° C and 3 ml. of trifluoroacetic acid is then added. The mixture is stirred vigorously for 3 minutes and then rapidly evaporated to dryness under reduced pressure. The resulting 3-(3-carbamoyloxyprop-1-(t)-enyl)-7β-(thiophen-2-ylacetamido)-ceph-3-em-4-carboxylic acid is dissolved in 10 ml. of tetrahydrofuran and then filtered. The filtrate is treated with 0.1 g. of sodium 2-ethylhexanoate and the resulting mixture evaporated to dryness. The residue is then treated with 5 ml. ethyl acetate and the heterogeneous mixture is stirred at room temperature for 30 minutes. The solid is collected by filtration, washed three times with ethyl acetate and then dried under vacuum to afford sodium 3-(3-carbamoyloxyprop-1-(t)-enyl)-7β-(thiophen-2-ylacetamido)-ceph-3-em-4-carboxylate which decomposes before melting; uv ($H_2O$): 291 nm ($\epsilon$ 18,800); ir (KBr): 1755, 1700, 1665, 1615 $cm^{-1}$; nmr (DMSO-$d_6$) δ: 3.43 (2H, bs); 3.73 (2H, s); 4.40 (2H, d, J6Hz); 4.98 (1H, d, J 4.5Hz); 5.48 (1H, dd, J 4.5, 8.5 Hz); 5.64 (1H, dt, J 15.5, 6 Hz); 6.43 (2H, bs); 6.8–7.4 (4H, m); 9.04 (1H, d, J 8.5Hz) ppm.

Similarly, by following the same procedure but using the products recited in paragraph 3 of Example 4 as starting materials, the following compounds are prepared:

3-[3-(N-methylcarbamoyloxy)prop-1-(t)-enyl]-7β-(thiophen-2-ylacetamido)-ceph-3-em-4-carboxylic acid, 3-[3-(N-ethylcarbamoyloxy)prop-1-(t)-enyl]-7β-(thiophen-2-ylacetamido)-ceph-3-em-4-carboxylic acid, 3-[3-(N-n-propylcarbamoyloxy)prop-1-(t)-enyl]-7β-(thiophen-2-ylacetamido)-ceph-3-em-4-carboxylic acid, 3-[3-(N-isopropylcarbamoyloxy)prop-1-(t)-enyl]-7β-(thiophen-2-ylacetamido)-ceph-3-em-4-carboxylic acid, 3-[3-(N-n-butylcarbamoyloxy)prop-1-(t)-enyl]-7β-(thiophen-2-ylacetamido)-ceph-3-em-4-carboxylic acid, 3-[3-(N-isobutylcarbamoyloxy)prop-1-(t)-enyl]-7β-(thiophen-2-ylacetamido)-ceph-3-em-4-carboxylic acid, 3-[3-(N-tert-butylcarbamoyloxy)prop-1-(t)-enyl]-7β-(thiophen-2-ylacetamido)-ceph-3-em-4-carboxylic acid, 3-[3-(N-n-pentylcarbamoyloxy)prop-1-(t)-enyl]-7β-(thiophen-2-ylacetamido)-ceph-3-em-4-carboxylic acid, 3-[3-(N-n-hexylcarbamoyloxy)prop-1-(t)-enyl]-7β-(thiophen-2-ylacetamido)-ceph-3-em-4-carboxylic acid, 3-[3-(N-benzylcarbamoyloxy)prop-1-(t)-enyl]-7β-(thiophen-2-ylacetamido)-ceph-3-em-4-carboxylic acid, 3-[3-(N-phenethylcarbamoyloxy)prop-1-(t)-enyl]-7β-(thiophen-2-ylacetamido)-ceph-3-em-4-carboxylic acid, 3-{3-[N-(3-phenylpropyl)carbamoyloxy]prop-1-(t)-enyl}-7β-(thiophen-2-ylacetamido)-ceph-3-em-4-carboxylic acid, 3-[3-(N-phenylcarbamoyloxy)prop-1-(t)-enyl]-7β-(thiophen-2-ylacetamido)-ceph-3-em-4-carboxylic acid, and the corresponding sodium salts, e.g., sodium [3-(N-methylcarbamoyloxy)prop-1-(t)-enyl]-7β-(thiophen-2-ylacetamido)-ceph-3-em-4-carboxylate, sodium [3-(N-ethylcarbamoyloxy)prop-1-(t)-enyl]-7β-(thiophen-2-acetamido)-ceph-3-em-4-carboxylate, sodium [3-(N-n-propylcarbamoyloxy)prop-1-(t)-enyl]-7β-(thiophen-2-ylacetamido)-ceph-3-em-4-carboxylate, sodium [3-(N-isopropylcarbamoyloxy)prop-1-(t)-enyl]-7β-(thiophen-2-ylacetamido)-ceph-3-em-4-carboxylate, sodium[3-(N-n-biutylcarbamoyloxy)prop-1-(t)-enyl]-7β-(thiophen -2ylacetamido)-cept-3-em-4-carboxylate, sodium[3-(N-isobutylcarbamoyloxy)prop-1-(t)-enyl]-7β-(thiophen-2-ylacetamido)-cepth-3-em-4-carboxylate, sodium[3-(N-tert-butylcarbamoyloxy)prop-1-(t)-enyl-7β-(thiophen-2-lyacetamido)-cept-3-em-4-carboxylate, sodium[3-(N-n-pentylcarbamoyloxy)prop-1-(t)-enyl-7β-(thiophen-2-ylacetamido)-ceph-3-em-4-carboxylate, sodium[3-(N-n-hexylcarbamoylosy)prop-1-(t)-enyl]-7β-(thiophen-2-ylacetamido)-ceph-3-em-4-carboxylate, sodium[3-(N-benzylcarbamoyloxy)prop-1-(t)-enyl]-7β-(thiophen-2-ylacetamido)-ceph-3-em-4-carboxylate, sodium[3-(N-phenethylcarbamoyloxy)prop-1-(t)-enyl]-7β-(thiophen-2yl -ylacetamido)-ceph-3-em-4-carboxylate, sodium{3-[N-(3-phenylpropyl)carbamoyloxy]prop-1-(t)-enyl}-7β-thiophen-2-ylacetamido)-ceph-3-em-4-carboxylate, and sodium[3-(n-phenylcarbamoyloxy)prop-1-(t)-enyl]-7β-(thiophen-2-ylacetamido)-ceph-3-em-4-carboxylate.

EXAMPLE 6

This example illustrates step 7 of the process of the invention. In this example a solution of 3.2 g of benzhydryl 3-(1-hydroxyprop-2-enyl)-7β-(thiophen-2-ylacetamido)-ceph-2-em-4-carboxylate in 10 ml. of tetrahydrofuran and 3 ml. of formic acid is stirred at 40° C and 50 mg. of p-toluenesulfonic acid added. After stirring for 6 hours, the mixture is poured into water and extracted three times with ethyl acetate. The ethyl acetate extracts are combined and then sequentially washed with water, excess dilute aqueous sodium bicarbonate solution and brine, and then dried over anhydrous sodium sulfate. The dried mixture is evaporated to dryness under reduced pressure. The residue is chromatographed on silica gel eluting with dichloromethane-/acetone 19:1 to afford benzhydryl 3-(3-formyloxyprop-1-(t)-enyl)-7β-(thiophen-2-ylacetamido)-ceph-2-em- 4-carboxylate as an oil; nmr ($CDCl_3$) δ: 3.78 (s, 2H); 4.49 (d, J 6 Hz, 2H); 5.18 (d, J 4 Hz 1H); 5.21 (s, 1H); 5.47 (dd, J 4, 9 Hz, 1H); 5.65 (dt, J 15, 6 Hz, 1H); 6.13 (d, J 15 Hz, 1H); 6.26 (s, 1H); 6.70 (d, J 9 Hz, 1H); 6.8–7.4 (m, 14H); 7.92 (s, 1H) ppm.

EXAMPLE 7

This example illustrates step 8 of the process of the invention. In this example a solution containing 0.84g. of benzhydryl 3-(3-formyloxyprop-1-(t)-enyl-7β-(thiophen-2-ylacetamido)-ceph-2-em-4-carboxylate in 25 ml. of dichoromethane is stirred at 0° C and m-chloroperbenzoic acid (0.25g.) is added in portions over 2 hours. The mixture is evaporated to dryness and the residue dissolved in ethyl acetate and washed three times with dilute aqueous sodium bicarbonate solution and brine. The solution is dried over anhydrous sodium sulfate and evaporated to dryness under reduced pressure. On mixing with ethyl ether, the residue deposits a solid which is collected by filtration and dried in vacuo to afford benzhydryl 3-(3-formyloxyprop-1-(t)-enyl)-7β-(thiophen-2-ylacetamido)-ceph-3-em-4-carboxylate-1-oxide, m.p. 153°–155° C.

EXAMPLE 8

This example illustrates step 9 of the process of the invention. In this example, a solution of 0.56g. of benzhydryl 3-(3-formyloxyprop-1-(t)-enyl)-7β-(thiophen-2-ylacetamido)-ceph-3-em-4-carboxylate-1-oxide in 10 ml.

of dimethylformamide is stirred under nitrogen at 0° C and stannous chloride (0.56g.) and acetyl chloride (1.1 ml.) are added. The mixture is stirred at 0° C for 15 minutes and then at room temperature (about 20° C) for 20 minutes. The mixture is then diluted with water and extracted three times with ethyl acetate. The combined ethyl acetate extracts are washed with brine, dried over anhydrous sodium sulfate and evaporated to dryness under reduced pressure. The residue is chromatographed on silica gel eluting with dichloromethane-/acetone 19:1 to afford benzhydryl 3-(3-formyloxyprop-1-(t)-enyl)-7β-(thiophen-2-ylacetamido)-ceph-3-em-4-carboxylate, m.p. 154°–156° C.

EXAMPLE 9

This example illustrates steps 10 and 11 of the process of the invention. In this example, 65 mg. of benzhydryl 3-(3-formyloxyprop-1-(t)-enyl)-7β-(thiophen-2-ylacetamido)-ceph-3-em-4-carboxylate and 0.5 ml. of anisole are stirred together at 0° C and approximately 3 ml. of trifluoroacetic acid is then added. The mixture is stirred at 0° C for 3 minutes and then evaporated to dryness. The resulting residue is dissolved in 15 ml. ethyl acetate and the solution is extracted twice with saturated aqueous sodium bicarbonate. The combined extracts are then allowed to stand at room temperature for 4 hours, after which the pH is adjusted to approximately 3 with concentrated hydrochloric acid. The mixture is then extracted three times with 10 ml. portions of ethyl acetate and the combined extracts are washed with brine, dried over sodium sulfate and filtered. The above obtained filtrate is then (a) evaporated to afford 3-(3-hydroxyprop-1-(t)-enyl)-7β-(thiophen-2-ylacetamido)-ceph-3-em-4-carboxylic acid; or (b) treated with an excess (0.1 g.) of 2-ethylhexanoate and the resulting solid collected by filtration, washed with ethyl acetate and dried under vacuum to afford sodium 3-(3-hydroxyprop-1-(t)-enyl)-7β-(thiophen-2-ylacetamido)-ceph-3-em-4-carboxylate which decmposes before melting [uv ($H_2O$): 291nm (δ 15,800); ir (KBr): 1760, 1665, 1605 $cm^{-1}$; nmr (DMSO-$d_6$) δ: 3.44 (2H, bs, 2-$CH_2$); 3.75 (2H, s); 3.95 (2H, d, J5Hz); 4.95 (1H, d J 3.5Hz); 5.44 (1H, dd, J 4.5, 8Hz); 5.68 (1H, dt, J 15.5, 5 Hz); 6.8–7.4 (4H, m); 9.03 (1H, d, J8Hz) ppm.]; or (c) treated with an excess of diphenyldiazomethane with warming and then evaporated and isolated using thick-layer chromatography on silica gel eluting with 1:10 acetone/methylene chloride to afford benzhydryl 3-(3-hydroxyprop-1-(t)-enyl)-7β-(thiophen-2-ylacetamido)-ceph-3-em-4-carboxylate; nmr ($CDCl_3$) δ: 3.21 (2H, ABq, J 16Hz); 3.80 (2H, s); 4.10 (2H, d, J 5.5Hz); 4.92 (1H, d, J 4.5Hz); 5.69 (1H, dd, J 4.5, 8.5Hz); 5.76 (1H, dt, J 15.5, 5.5Hz); 6.8–7.5 (16H, m) ppm.

EXAMPLE 10

This example illustrates steps 12 and 13 of the process of the invention. In this example 29 mg. of benzhydryl 3-(3-hydroxyprop-1-(t)-enyl)-7β-(thiophen-2-ylacetamido)-ceph-3-em-4-carboxylate in 5 ml. of tetrahydrofuran is stirred under nitrogen at −55° C and 15 μof chlorosulfonyl isocyanate is added. The mixture is then warmed to −20° C with stirring over a period of 30 minutes. Thereafter, 5 ml. of pH 7 buffer solution (sold by Scientific Products of McGaw Park, Ill.) is added and the mixture is warmed to 10° C with stirring over a period of 30 minutes. The reaction mixture is then diluted with 20 ml. of water and 20 ml. of ethyl acetate. The organic layer is then separated, washed with saturated aqueous sodium bicarbonate, then with brine and then dried over sodium sulfate and evaporated. The residue is purified using thick-layer chromatography on silica gel. Elution with 15% acetone in methylene chloride yields 10 mg. of product which is mixed with ether and filtered to afford benzhydryl 3-(3-carbamoyloxyprop-1-(t)-enyl)-7β-(thiophen-2-ylacetamido)-cpeh-3-em-4-carboxylate.

The above obtained ester and 0.5 ml. of anisole are stirred together at 0° C and 3 ml. of trifluoroacetic acid is then added. The mixture is stirred vigorously at 0° C for 3 minutes and then evaporated to dryness to afford 3-(3-carbamoyloxyprop-1-(t)-enyl)-7β-(thiophen-2-ylacetamido)-ceph-3-em-4-carboxylic acid.

The above obtained acid is dissolved in 10 ml. of tetrahydrofuran and then filtered. The filtrate is treated with 0.1 g. of sodium 2-ethylhexanoate and then evaporated to dryness. Ethyl acetate (5 ml.) is added to the residue and the mixture is then stirred for 30 minutes. The resulting solid is collected by filtration, washed three times with ethyl acetate and dried to afford sodium 3-(3-carbamoyloxyprop-1-(t)-enyl)-7β-(thiophen-2-ylacetamido)-ceph-3-em-4-carboxylate.

Moreover, by repeating the procedure of Example 3A but replacing benzhydryl 3-(3-hydroxyprop-1-(t)-enyl)-7β-(thiophen-2-ylacetamido)-ceph-2-em-4-carboxylate with benzhydryl 3-(3-hydroxyprop-1-(t)-enyl)-7β-(thiophen-2-ylacetamido)-ceph-3-em-4-carboxylate is productive of the N-substituted compounds previously prepared via Examples 4 and 5.

EXAMPLE 11

This example illustrates step 14 of the process of the invention. In this example a solution of 3.2 g. of benzhydryl 3-(1-hydroxyprop-2-enyl)-7β-(thiophen-2-ylacetamido)-ceph-2-em-4-carboxylate in 10 ml. of tetrahydrofuran and 10 ml. of acetic acid is stirred at 40° C and 50 mg. of p-toluenesulfonic acid added. After stirring for 6 hours, the mixture is poured into water and extracted three times with ethyl acetate. The ethyl acetate extracts are combined and then sequentially washed with water, excess dilute aqueous sodium bicarbonate solution and brine, and then dried over anhydrous sodium sulfate. The mixture is evaporated to dryness under reduced pressure affording 3.1 g of a yellow oil which is chromatographed on silica gel eluting with dichloromethane/acetone 19:1. The homogeneous fractions, by thin-layer chromatography, are combined to give 1.5 g. of benzhydryl 3-(3-acetoxyprop-1-(t)-enyl)-7β-(thiophen-2-ylacetamido)-ceph-2-em-4-carboxylate as a pale yellow oil; nmr ($CDCl_3$): 1.98 (s, 3H); 3.82 (s, 2H); 4.43 (d, J 5.5 Hz, 2H); 5.22 (d, J 4.0 Hz, 1H); 5.25 (s, 1H (4-H; 5.52dd, J 4, 8 Hz, 1H); 5.68 (dt, J 5.5, 15 Hz, 1H); 6.18 (d, J 15 Hz, 1H); 6.30 (s, 1H); 6.65 (d, J 8 Hz, 1H); 6.8–7.5 (m, 14H) ppm.

EXAMPLE 12

This example illustrates step 15 of the process of the invention. In this example a solution containing 1.5 g. of benzhydryl 3-(3-acetoxyprop-1-(t)-enyl)-7β-(thiophen-2-ylacetamido)-ceph-2-em-4-carboxylate in 50 ml. of dichloromethane is stired at 0° C and m-chloroperbenzoic acid (0.5 g.) is added in portions over 2 hours. The mixture is evaporated to dryness and the residue dissolved in ethyl acetate and washed three times with dilute aqueous sodium bicarbonate solution and brine.

The solution is dried over anhydrous sodium sulfate and evaporated to dryness under reduced pressure. On mixing with ethyl ether, the residue deposits a white solid which is collected by filtration and dried in vacuo to give 0.9 g. of benzyhydryl 3-(3-acetoxyprop-1-(t)-enyl)-7β-(thiophen-2-ylacetamido)-ceph-3-em-4-carboxylate-1-oxide as a white crystalline solid, m.p. 209°–211° C.

EXAMPLE 13

This example illustrates step 16 of the process of the invention. In this example, a solution of 0.5 g. of benzhydryl 3-(3-acetoxypropy-1-(t)-enyl)-7β-(thiophen-2-ylacetamido)ceph-3-em-4-carboxylate-1-oxide in oxide in 10 ml. of dimethylformamide is stirred under nitrogen at 0° C and stannous chloride (0.5 g.) and acetyl chloride (1 ml.) are added. The mixture is stirred at 0° C for 15 minutes and then at room temperature (about 20° C) for 20 minutes. The mixture is then diluted with water and extracted three times with ethyl acetate. The combined ethyl acetate extracts are washed with brine, dried over anhydrous sodium sulfate and evaporated to dryness under reduced pressure to give 0.55 g. of a yellow oil. This oil is chromatographed on silica gel eluting with dichlormethane/acetone 19:1 affording 0.4 g. of benzhydryl 3-(3-acetoxyprop-1-(t)-enyl)-7β-(thiophen-2-ylacetamido)-ceph-3-em-4-carboxylate as a white crystalline solid, m.p. 162°–164° C.

EXAMPLE 14

This example illustrates step 17 of the process of the invention. In this example a solution of 200 mg. of benzhydryl 3-(3-acetoxyprop-1-(t)-enyl)-7β-(thiophen-2-ylacetamido)ceph-3-em-4-carboxylate in 5 ml. of dichloromethane is stirred at room temperature under nitrogen and 52 mg. of pyridine and 135 mg. of phosphorous pentachloride are then added. The mixture is stirred at room temperature for three hours, then cooled to 0° C and treated with 0.1 ml. of isobutanol. After stirring for 1 hour, 0.25 ml. of water is added and the mixture stirred vigorously for 15 minutes. The mixture is then diluted with excess dilute aqueous sodium bicarbonate solution and extracted twice with ethyl acetate. The combined ethyl acetate extracts are washed with brine, dried over anhydrous sodium sulfate and evaporated to dryness under reduced pressure, giving benzhydryl 3-(3-acetoxyprop-1-(t)-enyl)-7β-aminoceph-3-em-4-carboxylate as a brown oil, nmr (CDCl$_3$): 1.99 (s, 3H); 3.55 (bd, 2H); 4.51 (d, J 6 Hz, 2H); 4.75 (d, J 5 Hz, 1H); 4.96 (d, J 5 Hz, 1H); 5.92 (dt, J 6, 16 Hz, 1H); 6.84 (d, J 16 Hz, 1H); 7.0–7.6 (m, 11H) ppm.

EXAMPLE 15

This example illustrates step 18 of the process of the invention. In this example a mixture of 0.1 g. of benzyhydryl 3-(3-acetoxyprop-1-(t)-enyl)-7β-aminoceph-3-em-4-carboxylate, 0.2 g. of tetrazol-1-acetic acid and 0.2 g. of dicyclohexylcarbodiimide in 10 ml. of dichloromethane is stirred for 2 hours at room temperature, and then a solution of 0.2 g. of oxalic acid in 3 ml. of methanol is added. After 10 minutes, the mixture is filtered, and the solid washed with dichloromethane. The combined filtrate and washings are diluted with ethyl acetate and sequentially washed with dilute aqueous sodium bicarbonate solution and brine and then dried over anhydrous sodium sulfate. The solution is evaporated to dryness under reduced pressure affording a brown oil which is then purified using preparative thin-layer chromatogrphy on silica gel. Elution with dichloromethane/acetone 19:1, affords benzhydryl 3-[3-acetoxyprop-1-(t)-enyl]-7β-(1H-tetrazol-1-ylacetamido)-ceph-3-em4-carboxylate as a white solid: [α]$_D$−64° (dioxane); uv (EtOH); 299 nm (ε 16,100); ir (KBr): 1770, 1725, 1685 cm$^{-1}$; nmr (DMSO-d$_6$) δ: 1.94 (s, 3H); 3.65 (d, J 17 hz, 1H); 3.92 (d, J 17 Hz, 1H); 4.52 (d, J 5 Hz, 2H); 5.25 (d, J 4.5 Hz, 1H); 5.41 (s, 2H); 5.85 (dd, J 4.5, 9 Hz, 1H); 6.20 (dt. J 15, 5 Hz, 1H); 6.69 (d, J 15 Hz, 1H); 7.00 (s, 1H); 7.2–7.7 (m, 10H); 9.39 (s, 1H); 9.59 (d, J 9 Hz, 1H) ppm. Anal. Found: C, 58.44; H, 4.78; N, 14.29%. C$_{28}$H$_{26}$N$_6$O$_6$S requires C, 58.23; H, 4.56; N, 14.63%.

Similarly, by following the same procedure but using the reagents listed in Table C hereinbelow, in place of tetrazol-1-acetic acid, and using pyridine in place of dicyclohexylcarbodiimide, the corresponding compounds listed in Table D are prepared:

TABLE C cyanoacetyl chloride
phenylacetyl chloride
phenoxyacetyl chloride
α-(methoxymethoxy)α-phenylacetyl chloride
α-(tert-butoxycarbonylamino)-α-(4-methoxymethoxyphenyl) acetyl chloride
syn-2-methoxyimino(fur-2-yl)acetyl chloride
4-pyridylthioacetyl chloride

TABLE D benzhydryl 3-[3-acetoxyprop-1-(t)-enyl]-7β-(cyanoacetamido)-ceph-3-em4-carboxylate,
benzhydryl 3-[3-acetoxyprop-1-(t)-enyl]-7β-(phenylacetamido)-ceph-3-em-4-carboxylate,
benzhydryl 3-[3-acetoxyprop-1-(t)-enyl]-7β-(phenoxyacetamido)-ceph-3-em-4-carboxylate,
benzhydryl 3-[3-acetoxyprop-1-(t)-enyl]-7β-[α-(methoxymethoxy)-α-phenylacetamido]-ceph-3-em-4-carboxylate,
benzhydryl 3-[3-acetoxyprop-1-(t)-enyl]-7β-[α-(tert-butoxycarbonylamino)-α-(4-methoxymethoxyphenyl) acetamido]-ceph-3-em-4-carboxylate,
benzhydryl 3-[3-acetoxprop-1-(t)-enyl]-7β-[2-methoxyimino-(fur-2-yl)acetamido]-ceph-3-em-4-carboxylate, and benzhydryl 3-[3-acetoxyprop-1-(t)-enyl]-7β[α-(4-pyridylthio)acetamido]-ceph-3-em-4-carboxylate.

EXAMPLE 15A

This example illustrates step 18 of the process of the invention. In this example 250 mg. of D-(−)-α-(t-butoxycarbonylamino)-α-phenylacetic acid in 2 ml. of dichloromethane and 200 mg. of dicyclohexylcarbodiimide are added to a solution of 200 mg. of benzhydryl 3-(3-acetoxyprop-1-(t)-enyl)-7β-aminoceph-3-em-4-carboxylate in 10 ml. of dichloromethane and the mixture stirred at room temperature for 2 hours. Thereafter, 2 ml. of a saturated solution of oxalic acid in methanol is added to the mixture. After 10 minutes the mixture is filtered and the collected solid washed with dichloromethane. The combined filtrate and washings are diluted with ethyl acetate, and then sequentially washed with aqueous sodium bicarbonate solution and brine, and then dried over anhydrous sodium sulfate. Evaporation of the mixture yields an oil which is purified by preparative thin-layer chromatography on silica gel. Elution with dichloromethane/acetone 19:1, gives 123 mg. of benzhydryl 3-(3-acetoxyprop-1-(t)-enyl)-7β-D-(α-t-butoxycarbonylamino-α-phenylacetamido)-ceph-3-em-4-carboxylate as an off-white solid; nmr (CDCl$_3$):

1.39 (s, 9H); 1.97 (s, 3H); 3.40 (s, 2H); 4.48 (d, J 6 Hz, 2H); 4.91 (d, J 5 Hz, 1H); 5.20 (d, J 6 Hz, 1H); 5.5–6.0 (m, 2H); 688 (d, J 16 Hz, 1H); 6.97 (s, 1H); 7.2–7.6 (m, 15H) ppm.

EXAMPLE 15B

This example illustrates step 18 of the process of the invention. In this example 0.15 g. of dicyclohexylcarbodiimide and 0.1 g. of α-(t-butoxycarbonyl)-phenyl acetic acid are added to a stirred solution of 0.15 g. of benzhydryl 3-(3-acetoxyprop-1-(t)-enyl)-7β-aminoceph-3-em-4-carboxylate in 5 ml. of dichloromethane. The mixture is stirred at room temperature for three hours, then filtered and the solids collected and washed with dichloromethane. The filtrate and washings are combined and evaporated to dryness. The residue is purified using preparative thin-layer chromatography on silica gel. Elution with dichloromethane/acetone, 19:1 vol., affords benzhydryl 3-(3-acetoxyprop-1-(t)-enyl)-7β-[α-(t-butoxycarbonyl)-α-phenylacetamido]-ceph-3-em-4-carboxylate.

EXAMPLE 16

This example illustrates step 19 of the process of the invention. In this example, 1 ml. of saturated aqueous sodium bicarbonate is added to a solution of 0.25 g. of benzhydryl 3-(3-acetoxyprop-1-(t)-enyl)-7β-[α-(tert-butoxycarbonyl)-α-phenylacetamido]-ceph-3-em-4-carboxylate in 3 ml. tetrahydrofuran. The mixture is allowed to stand for 8 hours at 35° C and is then diluted with water and extracted with 20 ml. of ethyl acetate. The extract is washed with water, dried over sodium sulfate and evaporated to dryness under reduced pressure. The residue is purified using thick-layer chromatography on silica gel. Elution with 10% acetone in methylene chloride affords benzhydryl 3-(3-hydroxyprop-1-(t)-enyl)-7β-[α-(tert-butoxycarbonyl)-α-phenylacetamido]-ceph-3-em-4-carboxylate.

Similarly, by following the same procedure but using the products obtained in Examples 15 and 15A as starting materials, the following compounds are prepared:
benzhydryl 3-(3-hydroxyprop-1-(t)-enyl)-7β-(1H-tetrazol-1-ylacetamido)-ceph-3-em-4-carboxylate,
benzhydryl 3-(3-hydroxyprop-1-(t)-enyl)-7β-(cyanoacetamido)-ceph-3-em-4-carboxylate,
benzhydryl 3-(3-hydroxyprop-1-(t)-enyl)-7β-(phenylacetamido)-ceph-3-em-4-carboxylate,
benzhydryl 3-(3-hydroxyprop-1-(t)-enyl)-7β-(phenoxyacetamido)-ceph-3-em-4-carboxylate,
benzhydryl 3-(3-hydroxyprop-1-(t)-enyl)-7β-[α-(methoxymethoxy)-α-phenylacetamido]-ceph-3-em-74-carboxylate,
benzhydryl 3-(3-hydroxyprop-1-(t)-enyl)-7β-[α-(tert-butoxycarbonylamino)-α-(4-methoxymethoxyphenyl)acetamido]-ceph-3-em-4-carboxylate,
benzhydryl 3-(3-hydroxyprop-1-(t)-enyl)-7β-[2-methoxyimino-(fur-2-yl)acetamido]-ceph-3-em-4-carboxylate,
benzhydryl 3-(3-hydroxyprop-1-(t)-enyl)-7β-[α-(4-pyridylthio)acetamido]-ceph-3-em-4-carboxylate, and
benzhydryl 3-(3-hydroxyprop-1-(t)-enyl)-7β-D-[α-(tert-butoxycarbonylamino)-α-phenylacetamido]-ceph-3-em-4-carboxylate.

EXAMPLE 17

This example illustrates step 20 of the process of the invention for preparing compounds of formula II' wherein R is hydrogen. In this example a solution of 80 mg. of benzhydryl 3-(3-hydroxyprop-1-(t)-enyl)-7β-(1H-tetrazol-1-ylacetamido)-ceph-3-em-4-carboxylate in 5 ml. of dry tetrahydrofuran is stirred under nitrogen at −50° C and 40 μl. of chlorosulfonyl isocyanate is added. Stirring is continued for 1 hour while the mixture is warmed to −20° C. Thereafter, 5 ml. of pH 7 buffer (sold by Scientific Products of McGaw Park, Ill.) and 25 ml. of ethyl acetate are added and the mixture is stirred for 15 minutes at room temperature. The ethyl acetate layer is then separated, washed with brine, dried over sodium sulfate and evaporated. The resulting solid is chromatographed on silica gel eluting with acetone/dichloromethane 1:10 to afford benzhydryl 3-(3-carbamoyloxyprop-1-(t)-enyl)-7β-(1H-tetrazol-1-ylacetamido)-ceph-3-em-4-carboxylate.

Similarly, by following the same procedure but using the products obtained in Example 16 as starting materials, the following compounds are prepared:
benzhydryl 3-(3-carbamoyloxyprop-1-(t)-enyl)-7β-[α(-tert-butoxycarbonyl)-α-phenylacetamido]-ceph-3-em-4-carboxylate,
benzhydryl 3-(3-carbamoyloxyprop-1-(t)-enyl)-7β-(cyanoacetamido)-ceph-3-em-4-carboxylate,
benzhydryl 3-(3-carbamoyloxyprop-1-(t)-enyl)-7β-(phenylacetamido)-ceph-3-em-4-carboxylate,
benzhydryl 3-(3-carbamoyloxyprop-1-(t)-enyl)-7β-(phenoxyacetamido)-ceph-3-em-4-carboxylate,
benzhydryl 3-(3-carbamoyloxyprop-1-(t)-enyl)-7β-[α-(methoxymethoxy)-α-phenylacetamido-ceph-3-em-4-carboxylate.
benzhydryl 3-(3-carbamoyloxyprop-1-(t)-enyl)-7β-[α-(tert-butoxycarbonylamino)-α-(4-methoxymethoxyphenyl)acetamido]-ceph-3-em-4-carboxylate,
benzhydryl 3-(3-carbamoyloxyprop-1-(t)-enyl)-7β-[2-methoxyimino-(fur-2-yl)acetamido]-ceph-3-em-4-carboxylate,
benzhydryl 3-(3-carbamoyloxyprop-1-(t)-enyl)-7β-[4-pyridylthioacetamido]-ceph-3-em-4-carboxylate, and
benzhydryl 3-(3-carbamoyloxyprop-1-(t)-enyl)-7β-D-[α-(tert-butoxycarbonylamino)-α-phenylacetamido]-ceph-3-em-4-carboxylate.

EXAMPLE 18

This example illustrates step 20 of the process of the invention for preparing the compounds of formula II' wherein R is other than hydrogen. In this example 0.2 g. of benzhydryl 3-(3-hydroxyprop-1-(t)-enyl)-7β-(1H-tetrazol-1-ylacetamido)-ceph-3-em-4-carboxylate, 0.55 g. of phenyl isocyanate and 3 ml. of tetrahydrofuran are heated at 60° C for 8 hours. Thereafter the reaction mixture is diluted with water and extracted several times with ethyl acetate. The combined ethyl acetate extracts are washed with water, dried over sodium sulfate, and evaporated to dryness. The residue is chromatographed on silica gel eluting with 10% acetone in methylene chloride to afford benzhydryl 3-[3-(N-phenylcarbamoyloxy)prop-1-(t)-enyl]-7β-(1H-tetrazol-1-ylacetamido)-ceph-3-em-4-carboxylate.

Similarly, by following the same procedure but replacing phenylisocyanate with the reagents listed in Table A, of Example 3; and then replacing benzhydryl 3-(3-hydroxyprop-1-(t)-enyl)-7β-(1H-tetrazol-1-ylacetamido)-ceph-3-em-4-carboxylate with the products obtained in Example 16, the following compounds are prepared:

benzhydryl 3-[3-(N-methylcarbamoyloxy)prop-1-(t)-enyl]-7β-(1H-tetrazol-1-ylacetamido)-ceph-3-em-4-carboxylate,
benzhydryl 3-[3-(N-ethylcarbamoyloxy)prop-1-(t)-enyl]-7β-(1H-tetrazol-1-ylacetamido)-ceph-3-em-4-carboxylate,
benzhydryl 3-[3-(N-n-propylcarbamoyloxy)prop-1-(t)-enyl]-7β-(1H-tetrazol-1-ylacetamido)-ceph-3-em-4-carboxylate,
benzhydryl 3-[3-(N-isopropylcarbamoyloxy)prop-1-(t)-enyl]-7β-(1H-tetrazol-1-ylacetamido)-ceph-3-em-4-carboxylate,
benzhydryl 3-[3-(N-n-butylcarbamoyloxy)prop-1-(t)-enyl]-7β-(1H-tetrazol-1-ylacetamido)-ceph-3-em-4-carboxylate,
benzhydryl 3-[3-(N-isobutylcarbamoyloxy)prop-1-(t)-enyl]-7β-(1H-tetrazol-1-ylacetamido)-ceph-3-em-4-carboxylate,
benzhydryl 3-[3-(N-tert-butylcarbamoyloxy)prop-1-(t)-enyl]-7β-(1H-tetrazol-1-ylacetamido)-ceph-3-em-4-carboxylate,
benzhydryl 3-[3-(N-n-pentylcarbamoyloxy)prop-1-(t)-enyl]-7β-(1H-tetrazol-1-ylacetamido)-ceph-3-em-4-carboxylate,
benzhydryl 3-[3-(N-n-hexylcarbamoyloxy)prop-1-(t)-enyl]-7β-(1H-tetrazol-1-ylacetamido)-ceph-3-em-4-carboxylate,
benzhydryl 3-[3-(N-benzylcarbamoyloxy)prop-1-(t)-enyl]-7β-(1H-tetrazol-1-ylacetamido)-ceph-3-em-4-carboxylate,
benzhydryl 3-[3-(N-phenethylcarbamoyloxy)prop-1-(t)-enyl]-7β-(1H-tetrazol-1-ylacetamido)-ceph-3-em-4-carboxylate,
benzhydryl 3-{3-[N-(3-phenylpropyl)carbamoyloxy]-prop-1-(t)-enyl}-7β-(1H-tetrazol-1-ylacetamido)-ceph-3-em-4-carboxylate,
benzhydryl 3-[3-(N-methylcarbamoyloxy)prop-1-(t)-enyl]-7β-(cyanoacetamido)-ceph-3-em-4-carboxylate,
benzhydryl 3-[3-(N-ethylcarbamoyloxy)prop-1-(t)-enyl]-7β-(cyanoacetamino)-ceph-3-em-4-carboxylate,
benzhydryl 3-[3-(N-n-propylcarbamoyloxy)prop-1-(t)-enyl]-7β-(cyanoacetamido)-ceph-3-em-4-carboxylate,
benzhydryl 3-[3-(N-isopropylcarbamoyloxy)prop-1-(t)-enyl]-7β-(cyanoacetamido)-ceph-3-em-4-carboxylate,
benzhydryl 3-[3-(N-n-butylcarbamoyloxy)prop-1-(t)-enyl]-7β-(cyanoacetamido)-ceph-3-em-4-carboxylate,
benzhydryl 3-[3-(N-isobutylcarbamoyloxy)prop-1-(t)-enyl]-7β-(cyanoacetamido)-ceph-3-em-4-carboxylate,
benzhydryl 3-[3-(N-tert-butylcarbamoyloxy)prop-1-(t)-enyl]-7β-(cyanoacetamido)-ceph-3-em-4-carboxylate,
benzhydryl 3-[3-(N-n-pentylcarbamoyloxy)prop-1-(t)-enyl]-7β-(cyanoacetamido)-ceph-3-em-4-carboxylate, benzhydryl 3-[3-(N-n-hexylcarbamoyloxy)prop-1-(t)-enyl]-7β-(cyanoacetamido)-ceph-3-em-4-carboxylate,
benzhydryl 3-[3-(N-benzylcarbamoyloxy)prop-1-(t)-enyl]-7β-(cyanoacetamido)-ceph-3-em-4-carboxylate,
benzhydryl 3-[3-(N-phenethylcarbamoyloxy)prop-1-(t)-enyl]-7β-(cyanoacetamido)-ceph-3-em-4-carboxylate,
benzhydryl 3-{3-[N-(3-phenylpropyl)carbamoyloxy]-prop-1-(t)-enyl}-7β-(cyanoacetamido)-ceph-3-em-4-carboxylate,
benzhydryl 3-[3-(N-phenylcarbamoyloxy)prop-1-(t)-enyl]-7β-(cyanoacetamido)-ceph-3-em-4-carboxylate,
benzhydryl 3-[3-(N-methylcarbamoyloxy)prop-1-(t)-enyl]-7β-(phenylacetamido)-ceph-3-em-4-carboxylate,
benzhydryl 3-[3-(N-ethylcarbamoyloxy)prop-1-(t)-enyl]-7β-(phenylacetamido)-ceph-3-em-4-carboxylate,
benzhydryl 3-[3-(N-n-propylcarbamoyloxy)prop-1-(t)-enyl-7β-(phenylacetamido)-ceph-3-em-4-carboxylate,
benzhydryl 3-[3-(N-isopropylcarbamoyloxy)prop-1-(t)-enyl]-7β-(phenylacetamido)-ceph-3-em-4-carboxylate,
benzhydryl 3-[3-(N-n-butylcarbamoyloxy)prop-1-(t)-enyl]-7β-(phenylacetamido)-ceph-3-em-4-carboxylate,
benzhydryl 3-[3-(N-isobutylcarbamoyloxy)prop-1-(t)-enyl]-7β-(phenylacetamido)-ceph-3-em-4-carboxylate,
benzhydryl 3-[3-(N-tert-butylcarbamoyloxy)prop-1-(t)-enyl]-7β-(phenylacetamido)-ceph-3-em-4-carboxylate,
benzhydryl 3-[3-(N-n-pentylcarbamoyloxy)prop-1-(t)-enyl]-7β-(phenylacetamido)-ceph-3-em-4-carboxylate,
benzhydryl 3-[3-(N-n-hexylcarbamoyloxy)prop-1-(t)-enyl]-7β-(phenylacetamido)-ceph-3-em-4-carboxylate,
benzhydryl 3-[3-(N-benzylcarbamoyloxy)prop-1-(t)-enyl]-7β-(phenylacetamido)-ceph-3-em-4-carboxylate,
benzhydryl 3-[3-(N-phenethylcarbamoyloxy)prop-1-(t)-enyl]-7β-(phenylacetamido)-ceph-3-em-4-carboxylate,
benzhydryl 3[3-[N-(3-phenylpropyl)carbamoyloxy]-prop-1-(t)-enyl]-7β-(phenylacetamido)-ceph-3-em-4-carboxylate,
benzhydryl 3-[3-(N-phenylcarbamoyloxy)prop-1-(t)-enyl]-7β-(phenylacetamido)-ceph-3-em-4-carboxylate,
benzhydryl 3-[3-(N-methylcarbamoyloxy)prop-1-(t)-enyl]-7β-(phenoxyacetamido)-ceph-3-em-4-carboxylate,
benzhydryl 3-[3-(N-ethylcarbamoyloxy)prop-1-(t)-enyl]-7β-(phenoxyacetamido)-ceph-3-em-4-carboxylate,
benzhydryl 3-[3-(N-n-propylcarbamoyloxy)prop-1-(t)-enyl]-7β-(phenoxyacetamido)-ceph-3-em-4-carboxylate,
benzhydryl 3[3-(N-isopropylcarbamoyloxy)prop-1-(t)-enyl]-7β-(phenoxyacetamido)ceph-3-em-4-carboxylate,
benzhydryl 3-[3-(N-n-butlycarbamoyloxy)prop-1-(t)-enyl]-7β-(phenoxyacetamido)-ceph-3-em-4-carboxylate,
benzhydryl 3-[3-(N-isobutylcarbamoyloxy)prop-1-(t)-enyl]-7β-(phenoxyacetamido)-ceph-3-em-4-carboxylate,
benzhydryl 3-[3-(N-tert-butylcarbamoyloxy)prop-1-(t)-enyl]-7β-(phenoxyacetamido)-ceph-3-em-4-carboxylate,
benzhydryl 3-[3-(N-n-pentylcarbamoyloxy)prop-1-(t)-enyl]-7β-(phenoxyacetamido)-ceph-3-4-carboxylate, benzhydryl 3-[3-(N-n-hexylcarbamoyloxy)prop-1-(t)-enyl]-7β-(phenoxyacetamido)-ceph-3-em-4-carboxylate, benzhydryl 3-[3-(N-benzylcarbamoyloxy)-prop-1-(t)-enyl]-7β-(phenoxyacetamido)-ceph-3-em-4-carboxylate, benzhydryl 3-[3-(N-phenethylcarbamoyloxy)prop-1-(t)-enyl]-7β-(phenoxyacetamido)ceph-3-em-4-carboxylate, benzhydryl 3-[3{3-[N-(3-phenylpropyl)carbamoyloxy]prop-1(t)-enyl]-7β-(phenoxyacetamido)-ceph-3-em-4-carboxylate, benzhydryl 3-[3-(N-phenylcarbamoyloxy)prop-1-(t)-enyl]-7β-(phenoxyacetamido)-ceph-3-em-4-carboxylate, benzhydryl 3-[3-(N-methylcarbamoyloxy)prop-1-(t)-enyl]-7β-[α-(methoxymethoxy)-α-phenylacetamido]-ceph-3-em-4-carboxylate, benzhydryl 3-[3-(N-ethylcarbamoyloxy)prop-1-(t)-enyl]-7β-[α-(methoxymethoxy)-α-phenylacetamido]-ceph-3-em-4-carboxylate, benzhydryl 3-[3-(N-n-propylcarbamoyloxy)prop-1-(t)-enyl]-7β-[α-(methoxymethoxy)-α-phenylacetamido]-ceph-3-em-4-carboxylate, benzhydryl 3-[3-(N-isopropylcarbamoyloxy)prop-1(t)-enyl]-7β-[α-(methoxymethoxy)-α-phenylacetamido]-ceph-3-em-4-carboxylate, benzhydryl 3-[3-(N-n-butylcarbamoyloxy)prop-1-(t)-enyl]-7β-[α-(methoxymethoxy)-α-phenylacetamido]-ceph-3-em-4-carboxylate, benzhydryl 3-[3-(N-isobutylcarbamoyloxy)prop-1-(t)-enyl]-7β-[α-(methoxymethoxy)-α-phenylacetamido]-ceph-3-em-4-carboxylate, benzhydryl 3-[3-(N-tert-butylcarbamoyloxy)prop-1-(t)-enyl]-7β[α-(methoxymethoxy)-α-phenylacetamido]-ceph-3-em-4-carboxylate, benzhydryl 3-[3-(N-n-pentylcarbamoyloxy)prop-1-(t)-enyl]-7β-[α-(methoxymethoxy)-α-phenylacetamido]-ceph-3-em-4-carboxylate, benzhydryl 3-[3-(N-n-hexylcarbamoyloxy)prop-1(t)-enyl]-7β-[α-(methoxymethoxy)-α-phenylacetamido]-ceph-3-em-4-carboxylate, benzhydryl 3-[3-(N-benzylcarbamoyloxy)prop-1-(t)-enyl]-7β-[α-(methoxymethoxy)-α-phenylacetamido]-ceph-3-em-4-carboxylate, benzhydryl 3-[3-(N-phenethylcarbamoyloxy)prop-1-(t)-enyl]-7β-[α-(methoxymethoxy)-α-phenylacetamido]-ceph-3-em-4-carboxylate, benzhydryl 3-{3-[N-(3-phenylpropyl)carbamoyloxy)-prop-1-(t)-enyl}-7β[α-(methoxymethoxy)-α-phenylacetamido]-ceph-3-em-4-carboxylate, benzhydryl 3-[3-(N-phenylcarbamoyloxy)prop-1-(t)-enyl]-7β-[α-(methoxymethoxy)-α-phenylacetamido]-ceph-3-em-4-carboxylate, benzhydryl 3-[3-(N-methylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-ethylcarbamoyloxy)prop-1-(t)-enyl]-7β-[α-(tert-butoxycarbonylamino)-α-(4methoxymethoxyphenyl)acetamido]-ceph-3-em-4-carboxylate, benzhydryl 3-[3-(N-n-propylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-isopropylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-n-butylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-isobutylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-tert-butylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-n-pentylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-n-hexylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-benzylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-[3-(N-phenethylcarbamoyloxy)prop-1-(t)-enyl]-7β-[α-(tert-butoxycarbonylamino)-α-(4-methoxymethoxyphenyl)acetamido]-ceph-3-em-4-carboxylate, benzhydryl 3-{3-[N-(3-phenylpropyl(carbamoyloxy]-prop-1-(t)-enyl}-7β-[α-(tert-butoxycarbonylamino)-α-(4-methoxymethoxyphenyl)acetamido]-ceph-3-em-4-carboxylate, benzhydryl 3-[3-(N-phenylcarbamoyloxy)prop-1-(t)-enyl]-7β-[α-tert-butoxycarbonylamino)-α-(4-methoxymethoxyphenyl)acetamido]-ceph-3-em-4-carboxylate, benzhydryl 3-[3-(N-methylcarbamoyloxy)prop-1-(t)-enyl]-7β-[2-methoxyimino-(fur-2-yl)acetamido]-ceph-3-em-4-carboxylate, benzhydryl 3-[3-(N-ethylcarbamoyloxy)prop-1-(t)-enyl]-7β-2-methoxyimino-(fur-2-yl)acetamido]-ceph-3-em-4-carboxylate, benzhydryl 3-[3-(N-n-propylcarbamoyloxy)prop-1-(t)-enyl]-7β-[2-methoxyimino-(fur-2-yl)-acetamido]-ceph-3-em-4-carboxylate, benzhydryl 3-3-(N-isopropylcarbamoyloxy)prop-1-(t)-enyl]-7β-[2-methoxyimino-(fur-2-yl)acetamido]-ceph-3-em-4-carboxylate, benzhydryl 3-[3-(N-n-butylcarbamoyloxy)prop-1-(t)-enyl]-7β-[2-methoxyimino-(fur-2-yl)acetamido]-ceph-3-em-4-carboxylate, benzhydryl 3-[3-(N-isobutylcarbamoyloxy)prop-1-(t)-enyl]-7β-2-methoxyimino-(fur-2-yl)acetamido]-ceph-3-em-4-carboxylate, benzhydryl 3-[3-(N-tert-butylcarbamoyloxy)prop-1-(t)-enyl]-7β-[2-methoxyimino-(fur-2-yl)acetamido]-ceph-3-em-4-carboxylate, benzhydryl 3-[3-(N-n-pentylcarbamoyloxy)prop-1-(t)-enyl]-7β-[2-methoxyimino-(fur-2-yl)acetamido]-ceph-3-em-4-carboxylate, benzhydryl 3-[3-(N-n-hexylcarbamoyloxy)prop-1-(t)-enyl]-7β-[2-methoxyimino-(fur-2-yl)acetamido]-ceph-3-em-4-carboxylate, benzhydryl 3-[3-(N-benzylcarbamoyloxy)prop-1-(t)-enyl]-7β-[2-methoxyimino-(fur-2-yl)acetamido]-ceph-3-em-4-carboxylate, benzhydryl 3-[3-(N-phenethylcarbamoyloxy)prop-1-(t)-enyl]-7β-[2-methoxyimino-(fur-2-yl)acetamido]-ceph-3-em-4-carboxylate,
benzhydryl 3-{3-[N-(3-phenylpropyl)carbamoyloxy]-prop-1-(t)-enyl}-7β-[2-methoxyimino-(fur-2-yl)acetamido]-ceph-3-em-4-carboxylate,
benzhydryl 3-[3-(N-phenylcarbamoyloxy)prop-1-(t)-enyl]-7β-[2-methoxyimino-(fur-2-yl)-acetamido]-ceph-3-em-4-carboxylate,
benzhydryl 3-[3-(N-methylcarbamoyloxy)prop-1-(t)-enyl]-7β-(4-pyridylthioacetamido)-ceph-3-em-4-carboxylate,
benzhydryl 3-(N-ethylcarbamoyloxy)prop-1-(t)-enyl]-7β-(4-pyridylthioacetamido)-ceph-3-em-4-carboxylate,
benzhydryl 3-[3-(N-n-propylcarbamoyloxy)prop-1-(t)-enyl]-7β-(4-pyridylthioacetamido)-ceph-3-em-4-carboxylate,
benzhydryl 3-[3-(N-isopropylcarbamoyloxy)prop-1-(t)-enyl]-7β-(4-pyridylthioacetamido)-ceph-3-em-4-carboxylate,
benzhydryl 3-[3-(N-n-butylcarbamoyloxy)prop-1-(t)-enyl]-7β-(4-pyridylthioacetamido)-ceph-3-em-4-carboxylate,
benzhydryl 3-[3-(N-isobutylcarbamoyloxy)prop-1-(t)-enyl]-7β-(4-pyridylthioacetamido)-ceph-3-em-4-carboxylate,
benzhydryl 3-[3-(N-tert-butylcarbamoyloxy)prop-1-(t)-enyl]-7β-(4-pyridylthioacetamido)-ceph-3-em-4-carboxylate,
benzhydryl 3-[3-(N-n-pentylcarbamoyloxy)prop-1-(t)-enyl]-7β-(4-pyridylthioacetamido)-ceph-3-em-4-carboxylate,
benzhydryl 3-[3-(N-n-hexylcarbamoyloxy)prop-1-(t)-enyl]-7β-(4-pyridylthioacetamido)-ceph-3-em-4-carboxylate,
benzhydryl 3-[3-(N-benzylcarbamoyloxy)prop-1-(t)-enyl]-7β-(4-pyridylthioacetamido)-ceph-3-em-4-carboxylate,
benzhydryl 3-[3-(N-phenethylcarbamoyloxy)prop-1-(t)-enyl]-7β-(4-pyridylthioacetamido)-ceph-3-em-4-carboxylate,
benzhydryl 3-{3-[N-(3-phenylpropyl)carbamoyloxy]-prop-1-(t)-enyl}-7β-(4-pyridylthio)acetamido]-ceph-3-em-4-carboxylate,
benzhydryl 3-[3-(N-phenylcarbamoyloxy)prop-1-(t)-enyl]-7β-(4-pyridylthioacetamido)-ceph-3-em-4-carboxylate,
benzhydryl 3-[3-(N-methylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-ethylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-n-propylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-isopropylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-n-butylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-isobutylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-tert-butylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-n-pentylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-n-hexylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-benzylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-phenethylcarbamoyloxy)prop-1-(t)-enyl]-7β-[α-(tert-butoxycarbonylamino)-α-phenylacetamido]-ceph-3-em-4-carboxylate,
benzhydryl 3-{3-[N-(3-phenylpropyl)carbamoyloxy]-prop-1-(t)-enyl}-7β-[α-(tert-butoxycarbonylamino)-α-phenylacetamido]-ceph-3-em-4-carboxylate,
benzhydryl 3-[3-(N-phenylcarbamoyloxy)prop-1-(t)-enyl]-7β-[α-(tert-butoxycarbonylamino)-α-phenylacetamido]-ceph-3-em-4-carboxylate,
benzhydryl 3-[3-(N-methylcarbamoyloxy)prop-1-(t)-enyl]-7β-[α-(tert-butoxycarbonyl)-α-phenylacetamido]-ceph-3-em-4-carboxylate,
benzhydryl 3-[3-(N-ethylcarbamoyloxy)prop-1-(t)-enyl]-7β-[α-(tert-butoxycarbonyl)-α-phenylacetamido]-ceph-3-em-4-carboxylate,
benzhydryl 3-[3-(N-n-propylcarbamoyloxy)prop-1-(t)-enyl]-7β-[α-(tert-butoxycarbonyl)-α-phenylacetamido]-ceph-3-em-4-carboxylate,
benzhydryl 3-[3-(N-isopropylcarbamoyloxy)prop-1-(t)-enyl]-7β-[α-(tert-butoxycarbonyl)-α-phenylacetamido]-ceph-3-em-4-carboxylate,
benzhydryl 3-[3-(N-n-butylcarbamoyloxy)prop-1-(t)-enyl]-7β-[α-(tert-butoxycarbonyl)-α-phenylacetamido]-ceph-3-em-4-carboxylate,
benzhydryl 3-[3-(N-isobutylcarbamoyloxy)prop-1-(t)-enyl-7β-[α-(tert-butoxycarbonyl)-α-phenylacetamido]-ceph-3-em-4-carboxylate,
benzhydryl 3-[3-(N-tert-butylcarbamoyloxy)prop-1-(t)-enyl]-7β-[α-(tert-butoxycarbonyl)-α-phenylacetamido]-ceph-3-em-4-carboxylate,
benzhydryl 3-[3-(N-n-pentylcarbamoyloxy)prop-1-(t)-enyl]-7β-[α-(tert-butoxycarbonyl)-α-phenylacetamido]-ceph-3-em-4-carboxylate,
benzhydryl 3-[3-(N-n-hexylcarbamoyloxy)prop-1-(t)-enyl]-7β-[α-(tert-butoxycarbonyl)-α-phenylacetamido]-ceph-3-em-4-carboxylate,
benzyhydryl 3-[3-(N-benzylcarbamoyloxy)prop-1-(t)-enyl]-7β-[α-(tert-butoxycarbonyl)-α-phenylacetamido]-ceph-3-em-4-carboxylate,
benzhydryl 3-[3-(N-phenylcarbamoyloxy)prop-1-(t)-enyl]-7β-[α-(tert-butoxycarbonyl)-α-phenylacetamido]-ceph-3-em-4-carboxylate,
benzhydryl 3-{3-[N-(3-phenylpropyl)carbamoyloxy]-prop-1-(t)-enyl}-7β-[α-(tert-butoxycarbonyl)-α-phenylacetamido]-ceph-3-em-4-carboxylate, and
benzhydryl 3-[3-(N-phenylcarbamoyloxy)prop-1-(t)-enyl]-7β-[α-(tert-butoxycarbonyl)-α-phenylacetamido]-ceph-3-em-4-carboxylate.

EXAMPLE 19

This example illustrates steps 21 and 22 of the process of the invention for preparing selected compounds of formulas II″ and III‴. In this example, 2.5 ml. of trifluoroacetic acid is added to a stirring mixture of 0.1 g. of benzhydryl 3-(3-hydroxyprop-1-(t)-enyl)-7β-(phenylacetamido)-ceph-3-em-4-carboxylate and 0.5 ml.

of anisole at 0° C. Stirring is continued at 0° C for approximately 2 minutes. The mixture is then evaporated to dryness under reduced pressure to afford 3-(3-hydroxyprop-1-(t)-enyl)-7β-(phenylacetamido)ceph-3-em-4-carboxylic acid.

The above obtained acid is dissolved in tetrahydrofuran, filtered and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum to afford sodium 3-(3-hydroxyprop-1-(t)-enyl)-7β-(phenylacetamido)-ceph-3-em-4-carboxylate.

Similarly, by following the same procedure but using the products of Examples 16, 17 and 18 wherein the 7β-substituent is

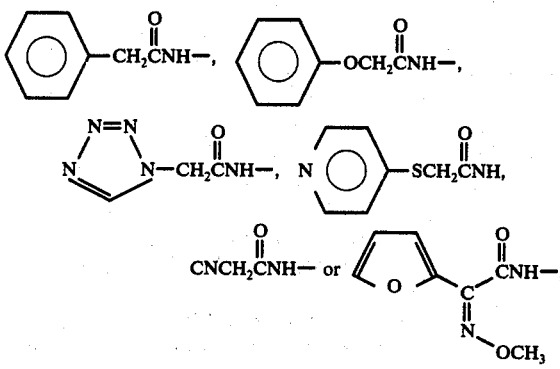

the following free acids and their pharmaceutically acceptable salts, including sodium salts, are prepared:

3-(3-hydroxyprop-1-(t)-enyl)-7β-(phenoxyacetamido)-ceph-3-em-4-carboxylic acid,
3-(3-hydroxyprop-1-(t)-enyl)-7β-[(1H)-tetrazol-1-ylacetamido]-ceph-3-em-4-carboxylic acid,
3-(3-hydroxyprop-1-(t)-enyl)-7β-[4-pyridylthioacetamido]-ceph-3-em-4-carboxylic acid,
3-(3-hydroxyprop-1-(t)-enyl)-7β-(cyanoacetamido)-ceph-3-em-4-carboxylic acid,
3-(3-hydroxyprop-1-(t)-enyl-7β-[2-methoxyimino-(fur-2-yl)acetamido]-ceph-3-em-4-carboxylic acid,
3-(3-carbamoyloxyprop)-1-(t)-enyl)-7β-(phenylacetamido)-ceph-3-em-4-carboxylic acid,
3-[3-(N-methylcarbamoyloxy)prop-1-(t)-enyl]-7β-(phenylacetamido)-ceph-3-em-4-carboxylic acid,
3-[3-(N-ethylcarbamoyloxy)prop-1-(t)-enyl]-7β-(phenylacetamido)-ceph-3-em-4-carboxylic acid,
3-[3-(N-n-propylcarbamoyloxy)prop-1-(t)-enyl]-7β-(phenylacetamido)-ceph-3-em-4-carboxylic acid,
3-[3-(N-isopropylcarbamoyloxy)prop-1-(t)-enyl]-7β-(phenylacetamido)-ceph-3-em-4-carboxylic acid,
3-[3-(N-n-butylcarbamoyloxy)prop-1-(t)-enyl]-7β-(phenylacetamido)-ceph-3-em-4-carboxylic acid,
3-[3-(N-isobutylcarbamoyloxy)prop-1-(t)-enyl]-7β-(phenylacetamido)-ceph-3-em-4-carboxylic acid,
3-[3-(N-tert-butycarbamoyloxy)prop-1-(t)-enyl]-7β-(phenylacetamido)-ceph-3-em-4-carboxylic acid,
3-[3-(N-n-pentylcarbamoxyloxy)prop-1-(t)-enyl]-7β-(phenylacetamido)-ceph-3-em-4-carboxylic acid,
3-[3-(N-n-hexylcarbamoyloxy)prop-1-(t)-enyl]-7β-(phenylacetamido)-ceph-3-em-4-carboxylic acid,
3-[3-(N-n-benzylcarbamoyloxy)prop-1-(t)-enyl]-7β-(phenylacetamido)-ceph-3-em-4-carboxylic acid,
3-[3-(N-n-phenethylcarbamoyloxy)prop1-(t)-enyl]-7β-(phenylacetamido)-ceph-3-em-4-carboxylic acid,
3-{3-[N-(3-phenylpropyl)carbamoyloxy]prop-1-(t)-enyl}-7β-(phenylacetamido)-ceph-3-em-4-carboxylic acid,
3-[3-(N-phenylcarbamoyloxy)prop-1-(t)-enyl]-7β-(phenylacetamido)-ceph-3-em-4-carboxylic acid,
3-(3-carbamoyloxyprop-1-(t)-enyl)-7β-(phenoxyacetamido)-ceph-3-em-4-carboxylic acid,
3-[3-(N-methylcarbamoyloxy)prop-1-(t)-enyl]-7β-(phenoxyacetamido)-ceph-3-em-4-carboxylic acid,
3-[3-N-ethylcarbamoyloxy)prop-1-(t)-enyl]-7β-(phenoxyacetamido)-ceph-3-em-4-carboxylic acid,
3-[3-(N-n-propylcarbamoyloxy)prop-1-(t)-enyl]-7β-(phenoxyacetamido)-ceph-3-em-4-carboxylic acid,
3-[3-(N-isopropylcarbamoyloxy)prop-1-(t)-enyl]-7β-(phenoxyacetamido)-ceph-3-em-4-carboxylic acid,
3-[3-(N-n-butylcarbamoyloxy)prop-1-(t)-enyl]-7β-(phenoxyacetamido)-ceph-3-em-4-carboxylic acid,
3-[3-(N-isobutylcarbamoyloxy)prop-1-(t)-enyl]-7β-(phenoxyacetamido)-ceph-3-em-4-carboxylic acid,
3-[3-(N-tert-butylcarbamoyloxy)prop-1-(t)-enyl]-7β-(phenoxyacetamido)-ceph-3-em-4-carboxylic acid,
3-[3-(N-n-pentylcarbamoyloxy)prop-1-(t)-enyl]-7β-(phenoxyacetamido)-ceph-3-em-4-carboxylic acid,
3-[3-(N-n-hexylcarbamoyloxy)prop-1-(t)-enyl]-7β-(phenoxyacetamido)-ceph-3-em-4-carboxylic acid,
3-[3-N-benzylcarbamoyloxy)prop-1-(t)-enyl]-7β-(phenoxyacetamido)-ceph-3-em-4-carboxylic acid,
3-[3-(N-phenethylcarbamoyloxy)prop-1-(t)-enyl]-7β-phenoxyacetamido)-ceph-3-em-4-carboxylic acid,
3-{3-[N-(3-phenylpropyl)carbamoyloxy]prop-1-(t)-enyl}-7β-phenoxyacetamido)-ceph-3-em-4-carboxylic acid,
3-[3-(N-phenylcarbamoyloxy)prop-1-(t)-enyl]-7β-(phenoxyacetamido)-ceph-3-em-4-carboxylic acid,
3-(3-carbamoyloxyprop-1-(t)-enyl-7β-[(1H)-tetrazol-1-ylacetamido]-ceph-3-em-4-carboxylic acid,
3-[3-(N-methylcarbamoyloxy)prop-1-(t)-enyl]-7β-[(1H)-tetrazol-1-ylacetamido]-ceph-3-em-4-carboxylic acid,
3-[3-(N-ethylcarbamoyloxy)prop-1-(t)-enyl]-7β-[(1H)-tetrazol-1-ylacetamido]-ceph-3-em-4-carboxylic acid,
3-[3-(N-n-propylcarbamoyloxy)prop-1-(t)-enyl]-7β-[(1H)-tetrazol-1-ylacetamido]-ceph-3-em-4-carboxylic acid,
3-[3-(N-isopropylcarbamoyloxy)prop-1-(t)-enyl]-7β-[(1H)-tetrazol-1-ylacetamido]-ceph-3-em-4-carboxylic acid,
3-[3-(N-n-butylcarbamoyloxy)prop-1-(t)-enyl]-7β-[(1H)-tetrazol-1-ylacetamido]-ceph-3-em-4-carboxylic acid,
3-[3-(N-isobutylcarbamoyloxy)prop-1-(t)-enyl]-7β-[(1H)-tetrazol-1-ylacetamido]-ceph-3-em-4-carboxylic acid,
3-[3-(N-tert-butylcarbamoyloxy)prop-1-(t)-enyl]-7β-[(1H)-tetrazol-1-ylacetamido]-ceph-3-em-4-carboxylic acid,
3-[3-(N-n-pentylcarbamoyloxy)prop-1-(t)enyl]-7β-[(1H)-tetrazol-1-ylacetamido]-ceph-3-em-4-carboxylic acid,
3-[3-(N-n-hexylcarbamoyloxy)prop-1-(t)-enyl]-7β-[(1H)-tetrazol-1-ylacetamido]-ceph-3-em-4-carboxylic acid,
3-[3-(N-benzylcarbamoyloxy)prop-1-(t)-enyl]-7β-[(1H)-tetrazol-1-ylacetamido]-ceph-3-em-4-carboxylic acid, 3-[3-(N-phenethylcarbamoyloxy)prop-1-(t)-enyl]-7β-[(1H)-tetrazol-1-ylacetamido]-ceph-3-em-4-carboxylic acid, 3-{3-[N-(3-phenylpropyl)carbamoyloxy]prop-1-(t)-enyl}-7β-[(1H)-tetrazol-1-ylacetamido]-ceph-3-em-4-carboxylic acid, 3-[3-(N-phenylcarbamoyloxy)prop-1-(t)-enyl]-7β-[(1H)-tetrazol-1-ylacetamido]-ceph-3-em-4-carboxylic acid, 3-(3-carbamoyloxyprop-1-(t)-enyl)-7β-(4-pyridylthioacetamido)-ceph-3-em-4-carboxylic acid, 3-[3-(N-methylcarbamoyloxy)prop-1-(t)-enyl]-7β-(4-pyridylthioacetamido)-ceph-3-em-4-carboxylic acid, 3-[3-(N-ethylcarbamoyloxy)prop-1-(t)-enyl]-7β-(4-pyridylthioacetamido)-ceph-3-em-4-carboxylic acid, 3-[3-(N-n-propylcarbamoyloxy)prop-1-(t)-enyl]-7β-(4-pyridylthioacetamido)-ceph-3-em-4-carboxylic acid, 3-[3-(N-isopropylcarbamoyloxy)prop-1-(t)-enyl]-7β-(4-pyridylthioacetamido)-ceph-3-em-4-carboxylic acid, 3-[3-(N-n-butylcarbamoyloxy)prop-1-(t)-enyl]-7β-(4-pyridylthioacetamido)-ceph-3-em-4-carboxylic acid, 3-[3-(N-isobutylcarbamoyloxy)prop-1-(t)-enyl]-7β-(4-pyridylthioacetamido)-ceph-3-em-4-carboxylic acid, 3-[3-(N-tert-butylcarbamoyloxy)prop-1-(t)-enyl]-7β-(4-pyridylthioacetamido)-ceph-3-em-4-carboxylic acid, 3-[3-(N-n-pentylcarbamoyloxy)prop-1-(t)-enyl]-7β-(4-pyridylthioacetamido)-ceph-3-em-4-carboxylic acid, 3-[3-(N-n-hexylcarbamoyloxy)prop-1-(t)-enyl]-7β-(4-pyridylthioacetamido)-ceph-3-em-4-carboxylic acid, 3-[3-(N-benzylcarbamoyloxy)prop-1-(t)-enyl]-7β-(4-pyridylthioacetamido)-ceph-3-em-4-carboxylic acid, 3-[3-(N-phenethylcarbamoyloxy)prop-1-(t)-enyl]-7β-(4-pyridylthioacetamido)-ceph-3-em-4-carboxylic acid, 3-{3-[N-(3-phenylpropyl)carbamoyloxy]prop-1-(t)-enyl}-7β-(4-pyridylthioacetamido)-ceph-3-em-4-carboxylic acid, 3-[3-(N-phenylcarbamoyloxy)prop-1-(t)-enyl]-7β-(4-pyridylthioacetamido)-ceph-3-em-4-carboxylic acid, 3-(3-carbamoyloxyprop-1-(t)-enyl)-7β-(cyanoacetamido)-ceph-3-em-4-carboxylic acid, 3-[3-(N-methylcarbamoyloxy)prop-1-(t)-enyl]-7β-(cyanoacetamido)-ceph-3-em-4-carboxylic acid, 3-[3-(N-ethylcarbamoyloxy)prop-1-(t)-enyl]-7β-(cyanoacetamido)-ceph-3-em-4-carboxylic acid, 3-[3-(N-n-propylcarbamoyloxy)prop-1-(t)-enyl]-7β-(cyanoacetamido)-ceph-3-em-4-carboxylic acid, 3-[3-(N-isopropylcarbamoyloxy)prop-1-(t)-enyl]-7β-(cyanoacetamido)-ceph-3-em-4-carboxylic acid, 3-[3-(N-n-butylcarbamoyloxy)prop-1-(t)-enyl]-7β-(cyanoacetamido)-ceph-3-em-4-carboxylic acid, 3-[3-(N-isobutylcarbamoyloxy)prop-1-(t)-enyl]-7β-(cyanoacetamido)-ceph-3-em-4-carboxylic acid, 3-[3-(N-tert-butylcarbamoyloxy)prop-1-(t)-enyl]-7β-(cyanoacetamido)-ceph-3-em-4-carboxylic acid, 3-[3-(N-n-pentylcarbamoyloxy)prop-1-(t)-enyl]-7β-(cyanoacetamido)-ceph-3-em-4-carboxylic acid, 3-[3-(N-n-hexylcarbamoyloxy)prop-1-(t)-enyl]-7β-(cyanoacetamido)-ceph-3-em-4-carboxylic acid, 3-[3-(N-benzylcarbamoyloxy)prop-1-(t)-enyl]-7β-(cyanoacetamido)-ceph-3-em-4-carboxylic acid, 3-[3-(N-phenethylcarbamoyloxy)prop-1-(t)-enyl]-7β-(cyanoacetamido)-ceph-3-em-4-carboxylic acid, 3-{3-[N-(3-phenylpropyl)carbamoyloxy]prop-1-(t)-enyl}-7β-(cyanoacetamido)-ceph-3-em-4-carboxylic acid, 3-[3-(N-phenylcarbamoyloxy)prop-1-(t)-enyl]-7β-(cyanoacetamido)-ceph-3-em-4-carboxylic acid, 3-(3-carbamoyloxyprop-1-(t)-enyl)-7β-[2-methoxyimino-(fur-2-yl)-acetamido]-ceph-3-em-4-carboxylic acid, 3-[3-(N-methylcarbamoyloxy)prop-1-(t)-enyl]-7β-[2-methoxyimino-(fur-2-yl)acetamido]-ceph-3-em-4-carboxylic acid, 3-[3-(N-ethylcarbamoyloxy)prop-1-(t)-enyl]-7β-[2-methoxyimino-(fur-2-yl)acetamido]-ceph-3-em-4-carboxylic acid, 3-[3-(N-n-propylcarbamoyloxy)prop-1-(t)-enyl]-7β-[2-methoxyimino-(fur-2-yl)acetamido]-ceph-3-em-4-carboxylic acid, 3-[3-(N-isopropylcarbamoyloxy)prop-1-(t)-enyl]-7β-[2-methoxyimino-(fur-2-yl)acetamido]-ceph-3-em-4-carboxylic acid, 3-[3-(N-n-butylcarbamoyloxy)prop-1-(t)-enyl]-7β-[2-methoxyimino-(fur-2-yl)acetamido]-ceph-3-em-4-carboxylic acid, 3-[3-(N-isobutylcarbamoyloxy)prop-1-(t)-enyl[-7β-[2-methoxyimino-(fur-2-yl)acetamido]-ceph-3-em-4-carboxylic acid, 3-[3-(N-tert-butylcarbamoyloxy)prop-1-(t)-enyl]-7β-[2-methoxyimino-(fur-2-yl)acetamido]-ceph-3-3-em-4-carboxylic acid, 3-[3-(N-n-pentylcarbamoyloxy)prop-1-(t)-enyl]-7β-[2-methoxyimino-(fur-2-yl)acetamido]-ceph-3-em-4-carboxylic acid, 3-[3-(N-n-hexylcarbamoyloxy)prop-1-(t)-enyl]-7β-[2-methoxyimino-(fur-2-yl)aeetamido]-ceph-3-em-4-4-carboxylic acid, 3-[3-(N-benzylcarbamoyloxy)prop-1-(t)-enyl]-7β-[2-methoxyimino-(fur-2-yl)acetamido]-ceph-3-em-4-carboxylic acid, 3-[3-(N-phenethylcarbamoyloxy)prop-1-(t)-enyl]-7β-[2-methoxyimino-(fur-2-yl)acetamido]-ceph-3-em-4-carboxylic acid, 3-{3-[N-(3-phenylpropyl)carbamoyloxy]prop-1-(t)-enyl}-7β-[2-methoxyimino-(fur-2-yl)acetamido]-ceph-3-em-4-carboxylic acid, and 3-[3-(N-phenylcarbamoyloxy)prop-1-(t)-enyl]-7β-[2-methoxyimino-(fur-2-yl)acetamido]-ceph-3-em-4-carboxylic acid.

EXAMPLE 20

This example illustrates steps 21 and 22 of the process of the invention for preparing selected compounds of formulas II″ and III″. In this example 2.5 ml. of trifluoroacetic acid is added to a mixture of 0.15 g. of benzhydryl 3-(3-hydroxyprop-1-(t)-enyl)-7β-[α-(tert-butoxycarbonylamino)-α-phenylacetamido]-ceph-3-em-4-carboxylate and 0.5 ml. of anisole at 0° C. The mixture is stirred for 30 minutes at 0° C and then evaporated to dryness to yield the trifluoroacetic acid salt of 3-(3-hydroxyprop-1-(t)-enyl)-7β-(α-amino-α-phenylacetamido)-ceph-3-em-4-carboxylic acid. The salt is mixed with 0.5 ml. of water and 0.5 ml. of a 25% solution of a water immiscible polymeric amine (sold under the Trademark Amberlite LA-1 (acetate form) by the Rohm and Haas Company of Philadelphia, Pennsylvania) in methylisobutyl ketone and the mixture is stirred for two hours at room temperature. The white solid which separates is collected by filtration and sequentially washed with 1:1 water/methylisobutyl ketone, methylisobutyl ketone and then acetone. Thereafter drying the product under vacuum affords 3-(3-hydroxyprop-1-(t)-enyl)-7β-(α-amino-α-phenylacetamido)-ceph-3-em-4-carboxylic acid.

The above obtained acid is dissolved in water, and is treated with one equivalent of 0.1 N sodium hydroxide solution. The mixture is evaporated to dryness. The residue is mixed with isopropanol and then filtered. The collected solid is washed several times with isopropanol and then dried under vacuum to afford sodium 3-(3-hydroxyprop-1-(t)-enyl)-7β-(α-amino-α-phenylacetamido)-ceph-3-em-4-carboxylate.

Similarly, by following the same procedure but using the products of Examples 17 and 18 wherein the 7β-substituent is

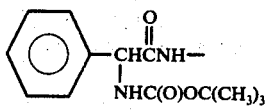

the following free acids and their pharmaceutically acceptable salts, including sodium salts are prepared:

3-[3-carbamoyloxyprop-1-(t)-enyl]-7β-(α-amino-α-phenylacetamido)-ceph-3-em-4-carboxylic acid,
3-[3-(N-methylcarbamoyloxy)prop-1-(t)-enyl]-7β-(α-amino-α-phenylacetamido)-ceph-3-em-4-carboxylic acid,
3-[3-(N-ethylcarbamoyloxy)prop-1-(t)-enyl]-7β-(α-amino-α-phenylacetamido)-ceph-3-em-4-carboxylic acid,
3-[3-(N-n-propylcarbamoyloxy)prop-1-(t)-enyl]-7β-(α-amino-α-phenylacetamido)-ceph-3-em-4-carboxylic acid,
3-[3-(N-isopropylcarbamoyloxy)prop-1-(t)-enyl]-7β-(α-amino-α-phenylacetamido)-ceph-3-em-4-carboxylic acid,
3-[3-(N-n-butylcarbamoyloxy)prop-1-(t)-enyl]-7β-(α-amino-α-phenylacetamido)-ceph-3-em-4-carboxylic acid,
3-[3-(N-isobutylcarbamoyloxy)prop-1-(t)-enyl]-7β-(α-amino-α-phenylacetamido)-ceph-3-em-4-carboxylic acid,
3-[3-(N-tert-butylcarbamoyloxy)prop-1-(t)-enyl]-7β-(α-amino-α-phenylacetamido)-ceph-3-em-4-carboxylic acid,
3-[3-(N-n-pentylcarbamoyloxy)prop-1-(t)-enyl]-7β-(α-amino-α-phenylacetamido)-ceph-3-em-4-carboxylic acid,
3-[3-(N-n-hexylcarbamoyloxy)prop-1-(t)-enyl]-7β-(α-amino-α-phenylacetamido)-ceph-3-em-4-carboxylic acid,
3-[3-(N-benzylcarbamlyloxy)prop-1-(t)-enyl]-7β-(α-amino-α-phenylacetamido)-ceph-3-em-4-carboxylic acid,
3-[3-(N-phenethylcarbamoyloxy)prop-1-(t)-enyl]-7β-(α-amino-α-phenylacetamido)-ceph-3-em-4-carboxylic acid,
3-{3-[N-(3-phenylpropyl)carbamoyloxy]prop-1-(t)-enyl}-7β-(α-amino-α-phenylacetamido)-ceph-3-em-4-carboxylic acid, and
3-[3-(N-phenylcarbamoyloxy)prop-1-(t)-enyl]-7β-(α-amino-α-phenylacetamido)-ceph-3-em-4-carboxylic acid.

EXAMPLE 21

This example illustrates steps 21 and 22 of the process of the invention for preparing selected compounds of formulas II″ and III″. In this example, a solution of 0.25 g. of benzhydryl 3-(3-hydroxyprop-1-(t)-enyl)-7β-[α-(tert-butoxycarbonyl)-α-phenylacetamido]-ceph-3-em-4-carboxylate in 0.5 ml. of anisole is cooled to 0° C and 3 ml. of trifluoroacetic acid is then added. The mixture is stirred for 30 minutes at 0° C and then evaporated to afford 3-(3-hydroxyprop-1-(t)-enyl)-7β-(α-carboxy-α-phenylacetamido-ceph-3-em-4-carboxylic acid.

The above obtained acid is dissolved in tetrahydrofuran, filtered and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum to afford the disodium salt of 3-(3-hydroxyprop-1-(t)-enyl)-7β-(α-carboxy-α-phenylacetamido)-ceph-3-em-4-carboxylic acid.

Similarly, by following the same procedure but using the products of Examples 17 and 18 wherein the 7β-substituent is

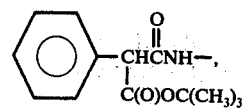

the following free acids and their pharmaceutically acceptable salts, including the disodium salts, are prepared:

3-[3-carbamoyloxyprop-1-(t)-enyl]-7β-(α-carboxy-α-phenylacetamido)-ceph-3-em-4-carboxylic acid.
3-[3-(N-methylcarbamoyloxy)prop-1-(t)-enyl]-7β(α-carboxy-α-phenylacetamido)-ceph-3-em-4-carboxylic acid,
3-[3-(N-ethylcarbamoyloxy)prop-1-(t)-enyl]-7β(α-carboxy-α-phenylacetamido)-ceph-3-em-4-carboxylic acid,
3-[3-(N-n-propylcarbamoyloxy)prop-1-(t)-enyl]-7β-(α-carboxy-α-phenylacetamido)-ceph-3-em-4-carboxylic acid,
3-[3-(N-isopropylcarbamoyloxy)prop-1-(t)-enyl]-7β-(α-carboxy-α-phenylacetamido)-ceph-3-em-4-carboxylic acid,
3-[3-(N-n-butylcarbamoyloxy)prop-1-(t)-enyl]-7β-(α-carboxy-α-phenylacetamido-ceph-3-em-4-carboxylic acid,
3-[3-(N-isobutylcarbamoyloxy)prop-1-(t)-enyl]-7β-(α-carboxy-α-phenylacetamido)-ceph-3-em-4-carboxylic acid,
3-[3-(N-tert-butylcarbamoyloxy)prop-1-(t)-enyl]-7β-(α-carboxy-α-phenylacetamido)-ceph-3-em-4-carboxylic acid,
3-[3-(N-n-pentylcarbamoyloxy)prop-1-(t)-enyl]-7β-(α-carboxy-α-phenylacetamido)-ceph-3-em-4-carboxylic acid,
3-[3-(N-n-hexylcarbamoyloxy)prop-1-(t)-enyl]-7β-(α-carboxy-α-phenylacetamido)-ceph-3-em-4-carboxylic acid,
3-[3-(N-benzylcarbamoyloxy)prop-1-(t)-enyl]-7β-(α-carboxy-α-phenylacetamido)-ceph-3-em-4-carboxylic acid,
3-[3-(Nphenethylcarbamoyloxy)prop-1-(t)-enyl]-7β-(α-carboxy-α-phenylacetamido)-ceph-3-em-4-carboxylic acid,
3-{3[N-(3-phenylpropyl)carbamoyloxy]prop-1-(t)-enyl}-7β-(α-carboxy-α-phenylacetamido)-ceph-3-em-4-carboxylic acid, and 3-[3-(N-phenylcarbamoyloxy)prop-1-(t)-enyl]-7β-(α-carboxy-α-phenylacetamido)-ceph-3-em-4-carboxylic acid.

EXAMPLE 22

This example illustrates steps 21 and 22 of the process of the invention for preparing selected compounds of formulas II″ and III″. In this example, 0.5 ml. of 0.1 N hydrochloric acid is added to a solution of 0.25 g. of benzhydryl 3-(3-hydroxyprop-1-(t)-enyl)-7β-(α-methoxymethoxy-α-phenylacetamido)-ceph-3-em-4-carboxylate in 2 ml. of tetrahydrofuran. The mixture is stirred for 5 minutes at room temperature and then evaporated to dryness. Thereafter the residue is dissolved in 0.5 ml. of anisole. The solution is then cooled to 0° C and 2.5 ml. of trifluoroacetic acid is added. The mixture is stirred for approximately 2 minutes at 0° C and then evaporated to afford 3-(3-hydroxyprop-1-(t)-enyl)-7β-(α-hydroxy-α-phenylacetamido)-ceph-3-em-4-carboxylic acid.

The above obtained acid is dissolved in tetrahydrofuran, filtered and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum to afford sodium 3-(3-hydroxyprop-1-(t)-enyl)-7β-(α-hydroxy-α-phenylacetamido)-ceph-3-em-4-carboxylate.

Similarly, by following the same procedure but using the products of Examples 17 and 18 wherein the 7β-substituent

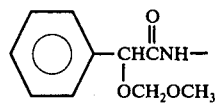

the following free acids and their pharmaceutically acceptable salts, including sodium salts, are prepared:

3-[3-carbamoyloxyprop-1-(t)-enyl]-7β-(α-hydroxy-α-phenylacetamido)-ceph-3-em-4-carboxylic acid,
3-[3-(N-methylcarbamoyloxy)prop-1-(t)-enyl]-7β-(α-hydroxy-α-phenylacetamido)-ceph-3-em-4-carboxylic acid,
3-[3-(N-ethylcarbamoyloxy)prop-1-(t)-enyl]-7β-(α-hydroxy-α-phenylacetamido)-ceph-3-em-4-carboxylic acid,
3-[3-(N-n-propylcarbamoyloxy)prop-1-(t)-enyl]-7β-(α-hydroxy-α-phenylacetamido)-ceph-3-em-4-carboxylic acid,
3-[3-(N-isopropylcarbamoyloxy)prop-1-(t)-enyl]-7β-(α-hydroxy-α-phenylacetamido)-ceph-3-em-4-carboxylic acid,
3-[3-(N-n-butylcarbamoyloxy)prop-1-(t)-enyl]-7β-(α-hydroxy-α-phenylacetamido)-ceph-3-em-4-carboxylic acid,
3-[3-(N-isobutylcarbamoyloxy)prop-1-(t)-enyl]-7β-(α-hydroxy-α-phenylacetamido)-ceph-3-em-4-carboxylic acid,
3-[3-(N-tert-butylcarbamoyloxy)prop-1-(t)-enyl]-7β-(α-hydroxy-α-phenylacetamido)-ceph-3-em-4-carboxylic acid,
3-[3-(N-n-pentylcarbamoyloxy)prop-1-(t)-enyl]-7β-(α-hydroxy-α-phenylacetamido)-ceph-3-em-4-carboxylic acid,
3-[3-(N-n-hexylcarbamoyloxy)prop-1-(t)-enyl]-7β-(α-hydroxy-α-phenylacetamido)-ceph-3-em-4-carboxylic acid,
3-[3(N-benzylcarbamoyloxy)prop-1(t)-enyl]-7β-(α-hydroxy-α-phenylacetamido)-ceph-3-em-4-carboxylic acid,
3-[3-(N-phenethylcarbamoyloxy)prop-2-(t)-enyl]-7β-(α-hydroxy-α-phenylacetamido)-ceph-3-em-4-carboxylic acid,
3-{3-[N-(3-phenylpropyl)carbamoyloxy]prop-1-(t)-enyl}-7β-(α-hydroxy-α-phenylacetamido)-ceph-3-em-4-carboxylic acid, and
3-[3-(N-phenylcarbamoyloxy)prop-1-(t)-enyl-7β-(α-hydroxy-α-phenylacetamido)-ceph-3-em-4-carboxylic acid.

EXAMPLE 23

This example illustrates steps 21 and 22 of the process of the invention for preparing certain compounds of formulas II″ and III″. In this example, 0.5 ml. of 0.1 N hydrochloric acid is added to a solution of 0.25 g. of benzhydryl 3-(3-hydroxypropyl-1-(t)-enyl)-7β-[α-tert-butoxycarbonylamino]-α-(4-methoxymethoxyphenyl)acetamido]-ceph-3-em-4-carboxylate in 2 ml. of tetrahydrofuran. After stirring for 5 minutes at room temperature, the solution is evaporated to dryness. The residue is dissolved in 0.5 ml. of anisole and the resulting solution cooled to 0° C. Thereafter, 2 ml. of trifluoroacetic acid is added to the solution and stirring is maintained for 30 minutes. The solution is then evaporated to dryness under reduced pressure to afford the trifluoroacetic acid salt of 3-(3-hydroxyprop-1-(t)-enyl)-7β-[α-amino-α-(4-hydroxyphenyl)acetamido]-ceph-3-em-4-carboxylic acid.

The above obtained salt is mixed with 0.5 ml. of water and 0.5 ml. of a 25% solution of a water immiscible polymeric amine (sold under the Trademark Amberlite LA-1 (acetate form) by the Rohm and Haas Company of Philadelphia, Pa.) in methyl isobutyl ketone. The mixture is stirred for two hours at room temperature. The white solid which separates is collected by filtration and sequentially washed with 1:1 water/methylisobutyl ketone, methylisobutyl ketone and then acetone. Therafter, drying the product under vacuum affords 3-(3-hydroxyprop-1-(t)-enyl)-7β-[α-amino-α-(4-hydroxyphenyl)acetamido]-ceph-3-em-4-carboxylic acid.

The above obtained acid is dissolved in water and treated with one equivalent of 0.1N sodium hydroxide solution. The mixture is evaporated to dryness. The residue is mixed with isopropanol and then filtered. The collected solid is washed several times with isopropanol and then dried under vacuum to afford sodium 3-(3-hydroxyprop-1-(t)-enyl)-7β-[α-amino-α-(4-hydroxyphenyl)acetamido]-ceph-3-em-4-carboxylate.

Similarly, by following the same procedure but using the products of Examples 17 and 18 wherein the 7β-substituent is

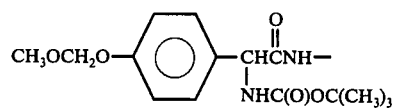

the following free acids and their pharmaceutically acceptable salts, including sodium salts are prepared:

3-[3-carbamoyloxyprop-1-(t)-enyl]-7β-[α-amino-α-(4-hydroxyphenyl)acetamido]-ceph-3-em-4-carboxylic acid, 3-[3-(N-methylcarbamoyloxy)prop-1-(t)-enyl]-7β-[α-amino-α-(4-hydroxyphenyl)acetamido]-ceph-3-em-4-carboxylic acid, 3-[3-(N-ethylcarbamoyloxy)prop-1-(t)-enyl]-7β-[α-amino-α-(4-hydroxyphenyl)acetamido]-ceph-3-em-4-carboxylic acid, 3-[3(N-n-propylcarbamoyloxy)prop-1-(t)-enyl]-7β-[α-amino-α-(4-hydroxyphenyl)acetamido]-ceph-3-em-4-carboxylic acid, 3-[3-(N-isopropylcarbamoyloxy)prop-1-(t)-enyl]-7β-[α-amino-α-(4-hydroxyphenyl)acetamido]-ceph-3-em-4-carboxylic acid, 3-[3-(N-n-butylcarbamoyloxy)prop-1-(t)-enyl]-7β-[α-amino-α-(4-hydroxphenyl)acetamido]-ceph-3-em-4-carboxylic acid, 3-[3-(N-isobutylcarbamoyloxy)prop-1-(t)-enyl]-7β-]α-amino-α-(4-hydroxyphenyl)acetamido]-ceph-3-em-4-carboxylic acid, 3-[3-(N-tert-butylcarbamoyloxy)prop-1-(t)-enyl-7β-[α-amino-α-(4-hydroxyphenyl)acetamido]-ceph-3-em-4-carboxylic acid, 3-[3-(N-n-pentylcarbamoyloxy)prop-1-(t)-enyl]-7β-[α-amino-α-(4-hydroxyphenyl)acetamido]-ceph-3-em-4-carboxylic acid, 3-[3-(N-n-hexylcarbamoyloxy)prop-1-(t)-enyl-]-7β-[α-amino-α-(4-hydroxyphenyl)acetamido]-ceph-3-em-4-carboxylic acid, 3-[3-(N-benzylcarbamoyloxy)prop-1-(t)-enyl]-7β-[α-amino-α-(4-hydroxyphenyl)acetamido]-ceph-3-em-4-carboxylic acid, 3-[3-(N-phenethylcarbamoyloxy)prop-1-(t)-enyl]-7β-[α-amino-α-(4-hydroxyphenyl)acetamido]-ceph-3-em-4-carboxylic acid, 3-{3-[N-(3-phenylpropyl)carbamoyloxy]prop-1-(t)-enyl}-7β-[α-amino-α-(4-hydroxyphenyl)acetamido]-ceph-3-em-4-carboxylic acid, and 3-[3-(N-phenylcarbamoyloxy)prop-1-(t)-enyl]-7β-[α-amino-α-(4-hydroxyphenyl)acetamido]-ceph-3-em-4-carboxylic acid.

EXAMPLE 24

This example illustrates replacement, if desired, of the C-4 carboxy protecting group in free acids of formulas II'' and III''. In this example, a solution of 0.2 g. of diphenyldiazomethane in 5 ml. of ethyl acetate is added to a solution of 3-(3-hydroxyprop-1-(t)-enyl)-7β-(α-hydroxy-α-phenylacetamido)-ceph-3-em-4-carboxylic acid in 50 ml. of ethyl acetate. The solution is stirred at 30° C for 3 hours and then evaporated to dryness. The resulting residue is chromatographed on silica gel. Elution with 90:10 methylene chloride:acetone affords benzhydryl 3-(3-hydroxyprop-1-(t)-enyl)-7β-(α-hydroxy-α-phenylacetamido)-ceph-3-em-4-carboxylate.

Similarly, by following the same procedure but replacing 3-(3-hydroxyprop-1-(t)-enyl-7β-(α-hydroxy-α-phenylacetamido)-ceph-3-em-4-carboxylic acid with other free acids embraced by the instant invention, the following C-4 esters are prepared:

benzhydryl 3-[3-hydroxyprop-1-(t)-enyl]-7β-(α-amino-α-phenylacetamido)-ceph-3-em-4-carboxylate, benzhydryl 3-[3-carbamoyloxyprop-1-(t)-enyl]-7β-(α-amino-α-phenylacetamido)-ceph-3-em-4-carboxylate, benzhydryl 3-[3-(N-methylcarbamoyloxy)prop-1-(t)-enyl]-7β-(α-amino-α-phenylacetamido)-ceph-3-em-4-carboxylate, benzhydryl 3-[3-(N-ethylcarbamoyloxy)prop-1-(t)-enyl]-7β-(α-amino-α-phenylacetamido)-ceph-3-em-4-carboxylate, benzhydryl 3-[3-(N-n-propylcarbamoyloxy)prop-1-(t)-enyl]-7β-(α-amino-α-phenylacetamido)-ceph-3-em-4-carboxylate, benzhydryl 3-[3-(N-isopropylcarbamoyloxy)prop-1-(t)-enyl]-7β-(α-amino-α-phenylacetamido)-ceph-3-em-4-carboxylate, benzhydryl 3-[3-(N-n-butylcarbamoyloxy)prop-1-(t)-enyl]-7β-(α-amino-α-phenylacetamido)-ceph-3-em-4-carboxylate, benzhydryl 3-[3-(N-isobutylcarbamoyloxy)prop-1-(t)-enyl]-7β-(α-amino-α-phenylacetamido)-ceph-3-em-4-carbocxylate, benzhydryl 3-[3-(N-tert-butylcarbamoyloxy)prop-1-(t)-enyl]-7β-(α-amino-α-phenylacetamido)-ceph-3-em-4-carboxylate, benzhydryl 3-[3-(N-n-pentylcarbamoyloxy)prop-1-(t)-enyl]-7β-(α-amino-α-phenylacetamido)-ceph-3-em-4-carboxylate, benzhydryl 3-[3-(N-n-hexylcarbamoyloxy)prop-1-(t)-enyl]-7β-(α-amino-α-phenylacetamido)-ceph-3-em-4-carboxylate, benzhydryl 3-[3-(N-benzylcarbamoyloxy)prop-1-(t)-enyl]-7β-(α-amino-α-phenylacetamido)-ceph-3-em-4-carboxylate, benzhydryl 3-[3-(N-phenethylcarbamoyloxy)prop-1-(t)-enyl]-7β-(α-amino-α-phenylacetamido)-ceph-3-em-4-carboxylate, benzhydryl 3-{3-[N-(3-phenylpropyl)carbamoyloxy]-prop-1-(t)-enyl}-7β-(α-amino-α-phenylacetamido)-ceph-3-em-4-carboxylate, benzhydryl 3-[3-(N-phenylcarbamoyloxy)prop-1-(t)-enyl]-7β-(α-amino-α-phenylacetamido)-ceph-3-em-4-carboxylate, benzhydryl 3-[3-carbamoyloxyprop-1-(t)-enyl]-7β-(α-hydroxy-α-phenylacetamido)-ceph-3-em-4-carboxylate, benzhydryl 3-[3-(N-methylcarbamoyloxy)prop-1-(t)-enyl]-7β-(α-hydroxy-α-phenylacetamido)-ceph-3-em-4-carboxylate, benzhydryl 3-[3-(N-ethylcarbamoyloxy)prop-1-(t)-enyl]-7β-(α-hydroxy-α-phenylacetamido)-ceph-3-em-4-carboxylate, benzhydryl 3-[3-(N-n-propylcarbamoyloxy)prop-1-(t)-enyl]-7β-(α-hydroxy-α-phenylacetamido)-ceph-3-em-4-carboxylate, benzhydryl 3-[3-(N-isopropylcarbamoyloxy)prop-1-(t)-enyl]-7β-(α-hydroxy-α-phenylacetamido)-ceph-3-em-4-carboxylate, benzhydryl 3-[3-(N-n-butylcarbamoyloxy)prop-1-(t)-enyl]-7β-(α-hydroxy-α-phenylacetamido)-ceph-3-em-4-carboxylate, benzhydryl 3-[3-(N-isobutylcarbamoyloxy)prop-1-(t)-enyl]-7β-(α-hydroxy-α-phenylacetamido)-ceph-3-em-4-carboxylate, benzhydryl 3-[3-(N-tert-butylcarbamoyloxy)prop-1-(t)-enyl]-7β-(α-hydroxy-α-phenylacetamido)-ceph-3-em-4-carboxylate, benzhydryl 3-[3-(N-n-pentylcarbamoyloxy)prop-1-(t)-enyl]-7β-(α-hydroxy-α-phenylacetamido)-ceph-3-em-4-carboxylate, benzhydryl 3-[3-(N-n-hexylcarbamoyloxy)prop-1-(t)-enyl]-7β-(α-hydroxy-α-phenylacetamido)-ceph-3-em-4-carboxylate, benzhydryl 3-[3-(N-benzylcarbamoyloxy)prop-1-(t)-enyl]-7β-(α-hydroxy-α-phenylacetamido)-ceph-3-em-4-carboxylate, benzhydryl 3-[3-(N-phenethylcarbamoyloxy)prop-1-(t)-enyl]-7β-(α-hydroxy-α-phenylacetamido)-ceph-3-em-4-carboxylate, benzhydryl 3-{3-[N-(3-phenylpropyl)carbamoyloxy]-prop-1-(t)-enyl}-7β-(α-hydroxy-α-phenylacetamido)-ceph-3-em-4-carboxylate, benzhydryl 3-[3-(N-phenylcarbamoyloxy)prop-1-(t)-enyl]-7β-(α-hydroxy-α-phenylacetamido)-ceph-3-em-4-carboxylate, benzhydryl 3-(3-hydroxyprop-1-(t)-enyl)-7β-[α-amino-α-(4-hydroxyphenyl)acetamido]-ceph-3-em-4-carboxylate, benzhydryl 3-[3-carbamoyloxyprop-1-(t)-enyl]-7β-[α-amino-α-(4-hydroxyphenyl)acetamido]-ceph-3-em-4-carboxylate, benzhydryl 3-[3-(N-methylcarbamoyloxy)prop-1-(t)-enyl]-7β-[α-amino-α-(4-hydroxyphenyl)acetamido]-ceph-3-em-4-carboxylate, benzhydryl 3-[3-(N-ethylcarbamoyloxy)prop-1-(t)-enyl]-7β-[α-amino-α-(4-hydroxyphenyl)acetamido]-ceph-3-em-4-carboxylate, -(4-hydroxyphenyl)acetamido]-cephbenzhydryl 3-[3-(N-n-propylcarbamoyloxy)prop-1-(t)-enyl]-7β-[α-amino-α-(4-hydroxyphenyl)acetamido]-ceph-3-em-4-carboxylate, benzhydryl 3-[3-(N-isopropylcarbamoyloxy)prop-1-(t)-enyl]-7β-[α-amino-α-(4-hydroxyphenyl)acetamido]-ceph-3-em-4-carboxylate, benzhydryl 3-[3-(N-n-butylcarbamoyloxy)prop-1-(t)-enyl]-7β-[α-amino-α-(4-hydroxyphenyl)acetamido]-ceph-3-em-4-carboxylate, benzhydryl 3-[3-(N-isobutylcarbamoyloxy)prop-1-(t)-enyl]-7β-[α-amino-α-(4-hydroxyphenyl)acetamido]-ceph-3-em-4-carboxylate, benzhydryl 3-[3-(N-tert-butylcarbamoyloxy)prop-1-(t)-enyl]-7β-[α-amino-α-(4-hydroxyphenyl)acetamido]-ceph-3-em-4-carboxylate, benzhydryl 3-[3-(N-n-pentylcarbamoyloxy)prop-1-(t)-enyl]-7β-[α-amino-α-(4-hydroxyphenyl)acetamido]-ceph-3-em-4-carboxylate, benzhydryl 3-[3-(N-n-hexylcarbamoyloxy)prop-1-(t)-enyl]-7β-[α-amino-α-(4-hydroxyphenyl)acetamido]-ceph-3-em-4-carboxylate, benzhydryl 3-[3-(N-benzylcarbamoyloxy)prop-1-(t)-enyl]-7β-[α-amino-α-(4-hydroxyphenyl)acetamido]-ceph-3-em-4-carboxylate, benzhydryl 3-[3-(N-phenethylcarbamoyloxy)prop-1-(t)-enyl]-7β-[α-amino-α-(4-hydroxyphenyl)acetamido]-ceph-3-em-4-carboxylate, benzhydryl 3-{3-[N-(3-phenylpropyl)carbamoyloxy]-prop-1-(t)-enyl}-7β-[α-amino-α-(4-hydroxyphenyl)acetamido]-ceph-3-em-4-carboxylate, benzhydryl 3-[3-(N-phenylcarbamoyloxy)prop-1-(t)-enyl]-7β-[α-amino-α-(4-hydroxyphenyl)acetamido]-ceph-3-em-4-carboxylate, and so forth.

EXAMPLE 25

For purposes of purifying and isolating the free acids of the invention, a small portion (10 mg.) of each of the sodium salt products, prepared according to Examples 19, 20, 21, 22 and 23, is converted to the corresponding 4-carboxylic acid by dissolving the salt in water, adjusting the pH to 1.5 using dilute hydrochloric acid and extracting twice with ethyl acetate. The combined extracts are washed with brine, dried and evaporated to dryness. The residue is mixed with ethyl ether and the purified 4-carboxylic acid product collected by filtration.

What is claimed is:
1. A compound having the formula:

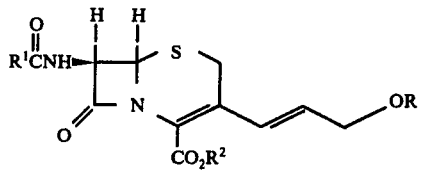

wherein
R is hydrogen or a group having the formula

in which $R^3$ is hydrogen, alkyl having one to six carbon atoms, or the group

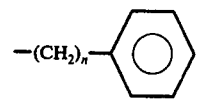

in which $n$ is 0 to 3, inclusive;
$R^1$ is a group having the formula

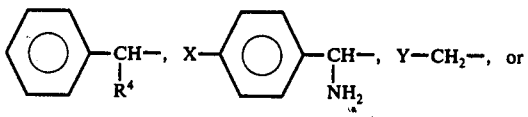

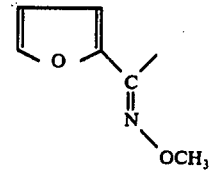

wherein $R^4$ is hydrogen, hydroxy or carboxy; X is hydrogen or hydroxy; Y is thiophen-2-yl, (1H)-tetrazol-1-yl, 4-pyridylthio, phenoxy or cyano; $R^2$ is hydrogen or a protecting group selected from the group of benzhydryl, benzyl, o-nitrobenzyl, p-nitrobenzyl, 3,5-dinitrobenzyl, p-methoxybenzyl, tert-butyl, pivaloyloxymethyl, phenacyl and polyhaloalkyl having two to six carbon atoms; and the pharmaceutically acceptable salts thereof.

2. A compound of claim 1 having the formula:

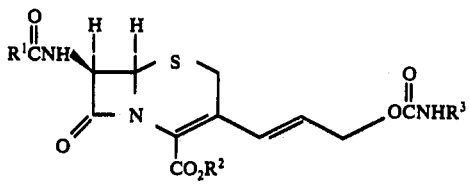

wherein $R^1$, $R^2$ and $R^3$ are as defined in claim 1, and the pharmaceutically acceptable salts thereof.

3. A compound of claim 2 wherein $R^3$ is hydrogen or phenyl.

4. A compound of claim 3 wherein $R^1$ is

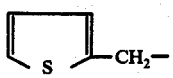

5. A compound of claim 4 wherein $R^2$ is benzhydryl.

6. The compound of claim 5 which is benzhydryl 3-(3-carbamoyloxyprop-1-(t)-enyl)-7β-(thiophen-2-ylacetamido)-ceph-3-em-4-carboxylate.

7. A compound of claim 4 wherein $R^2$ is hydrogen and pharmaceutically acceptable salts thereof.

8. The compound of claim 7 which is 3-(3-carbamoyloxyprop-1-(t-enyl)-7β-(thiophenyl-2-ylacetamido)-ceph-3-em-4-carboxylic acid and the pharmaceutically acceptable salts thereof.

9. The compound of claim 8 wherein said compound is a sodium salt.

10. The compound of claim 7 which is 3-[3-(N-phenylcarbamoyloxy)prop-1-(t)-enyl]-7β-(thiophen-2-ylacetamido)-ceph-3-em-4-carboxylic acid and the pharmaceutically acceptable salts thereof.

11. The compound of claim 10 wherein said compound is a sodium salt.

12. A compound of claim 3 wherein $R^1$ is

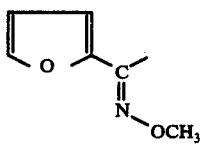

13. A compound of claim 12 wherein $R^2$ is benzhydryl.

14. A compound of claim 12 wherein $R^2$ is hydrogen and pharmaceutically acceptable salts thereof.

15. The compound of claim 14 which is 3-(3-carbamoyloxyprop-1-(t)-enyl)-7β-[2-methoxyimino-(fur-2-yl)acetamido]-ceph-3-em-4-carboxylic acid and the pharmaceutically acceptable salts thereof.

16. The compound of claim 15 wherein said compound is a sodium salt.

17. The compound of claim 14 which is 3-[3-(N-phenylcarbamoyloxy)prop-1-(t)-enyl]-7β-[2-methoxyimino-(fur-2-yl)acetamido]-ceph-3-em-4-carboxylic acid and the pharmaceutically acceptable salts thereof.

18. The compound of claim 17 wherein said compound is a sodium salt.

19. A compound of claim 3 wherein $R^1$ is

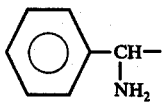

20. A compound of claim 19 wherein $R^2$ is benzhydryl.

21. A compound of claim 19 wherein $R^2$ is hydrogen and pharmaceutically acceptable salts thereof.

22. The compound of claim 21 which is 3-(3-carbamoyloxyprop-1-(t)-enyl)-7β-(α-amino-α-phenylacetamido)-ceph-3-em-4-carboxylic acid and the pharmaceutically acceptable salts thereof.

23. The compound of claim 22 wherein said compound is a sodium salt.

24. The compound of claim 21 which is 3-[3-(N-phenylcarbamoyloxy)prop-1-(t)-enyl]-7β-(α-amino-α-phenylacetamido)ceph-3-em-4-carboxylic acid and the pharmaceutically acceptable salts thereof.

25. The compound of claim 24 wherein said compound is a sodium salt.

26. A compound of claim 1 having the formula:

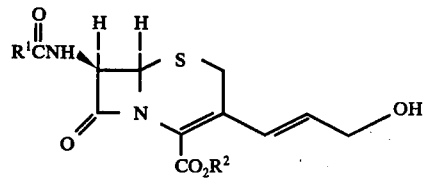

wherein $R^1$ and $R^2$ are as defined in claim 1, and the pharmaceutically acceptable salts thereof.

27. A compound of claim 26 wherein $R^1$ is

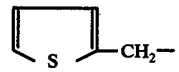

28. The compound of claim 27 which is benzhydryl 3-(3-hydroxyprop-1-(t)-enyl)-7β-(thiophen-2-ylacetamido)-ceph-3-em-4-carboxylate.

29. The compound of claim 28 which is 3-(3-hydroxyprop-1-(t)-enyl-7β-(thiophen-2-ylacetamido)-ceph-3-em-4-carboxylic acid and the pharmaceutically acceptable salts thereof.

30. The compound of claim 29 wherein said compound is a sodium salt.

31. A compound of claim 26 wherein $R^1$ is

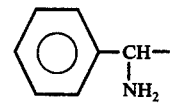

32. The compound of claim 1 wherein $R^2$ is benzhydryl.

33. The compound of claim 1 which is 3-(3-hydroxyprop-1-(t)-enyl-7β-(α-amino-α-phenylacetamido)-ceph-3-em-4-carboxylic acid and the pharmaceutically acceptable salts thereof.

34. The compound of claim 33 wherein said compound is a sodium salt.

35. An antibacterial composition comprising an effective amount of a compound of claim 2, or a pharmaceutically acceptable salt thereof, and mixtures of such compounds, with a pharmaceutically acceptable carrier.

36. An antibacterial composition comprising an effective amount of a compound of claim 26, or a pharmaceutically acceptable salt thereof, and mixtures of such compounds, with a pharmaceutically acceptable carrier.

* * * * *